United States Patent
Tan et al.

(10) Patent No.: US 12,257,361 B1
(45) Date of Patent: Mar. 25, 2025

(54) DETECTOR AND STERILIZATION SYSTEM

(71) Applicant: SHENZHEN MUXIN TECHNOLOGY CO., LTD., Shenzhen (CN)

(72) Inventors: Bo Tan, Shenzhen (CN); Chang Zhan, Shenzhen (CN); Xuanzhe Wei, Shenzhen (CN)

(73) Assignee: SHENZHEN MUXIN TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/802,057

(22) Filed: Aug. 13, 2024

Related U.S. Application Data

(63) Continuation of application No. PCT/CN2024/107519, filed on Jul. 25, 2024.

(30) Foreign Application Priority Data

Dec. 29, 2023 (CN) .......................... 202311862770.2

(51) Int. Cl.
*A61L 2/26* (2006.01)
*A61B 5/00* (2006.01)
*A61L 2/08* (2006.01)

(52) U.S. Cl.
CPC .............. *A61L 2/26* (2013.01); *A61B 5/6848* (2013.01); *A61L 2/081* (2013.01); *A61L 2/082* (2013.01); *A61L 2/087* (2013.01); *A61L 2202/11* (2013.01); *A61L 2202/121* (2013.01); *A61L 2202/122* (2013.01); *A61L 2202/123* (2013.01); *A61L 2202/24* (2013.01)

(58) Field of Classification Search
CPC . A61L 2/26; A61L 2/081; A61L 2/082; A61L 2/084; A61L 2202/11; A61L 2202/121; A61L 2202/122; A61L 2202/123; A61L 2202/24
See application file for complete search history.

(56) References Cited

U.S. PATENT DOCUMENTS

| | | | |
|---|---|---|---|
| 9,402,570 B2* | 8/2016 | Pace | A61B 5/150847 |
| 11,071,478 B2* | 7/2021 | Rao | A61B 5/6823 |
| 2021/0204841 A1 | 7/2021 | Thomas et al. | |
| 2022/0079475 A1* | 3/2022 | Cole | A61B 5/002 |
| 2022/0175281 A1* | 6/2022 | Chae | A61B 5/14532 |

* cited by examiner

*Primary Examiner* — David E Smith
(74) *Attorney, Agent, or Firm* — Daniel M. Cohn; Howard M. Cohn

(57) ABSTRACT

A detector includes a housing assembly, a detection assembly and a shielding assembly. The detection assembly includes a first housing, a detection circuit board and a probe, the detection circuit board is disposed in the first housing and electrically connected with the probe, the detection circuit board includes a sensitive element, and a first end of the probe is fixed in the first housing while a second end stretches out of the first housing; the housing assembly includes a collision housing and a pressing portion that are capable of sliding in relative to each other, the detection assembly is located below a bottom of the pressing portion, the collision housing is used for abutting against a sampling part, and the pressing portion is used for driving the detection assembly to move towards the sampling part, so as to pierce the probe into the sampling part for detection.

20 Claims, 44 Drawing Sheets

DETECTOR AND STERILIZATION SYSTEM

CROSS-REFERENCE TO RELATED APPLICATIONS

The present disclosure is a continuation-application of International (PCT) Patent Application No. PCT/CN2024/107519, field on Jul. 25, 2024, which claims priority of Chinese Patent Application No. 202311862770.2, field on Dec. 29, 2023, the entire contents of which are hereby incorporated by reference in their entirety.

TECHNICAL FIELD

The present disclosure relates to the technical field of health detection, and in particular to a detector and a sterilization system.

BACKGROUND

In a routine medical detection environment, when a to-be-detected object is subjected to subcutaneous sampling detection, the help of a detector is required. The detector usually includes a detection instrument for driving a guide needle to move, and when in detection, the guide needle and a probe are usually driven by the detector to pierce a sampling part, thus obtaining body indexes through a detection circuit board inside the detector. To guarantee the medical health, the detector must be sterilized before delivering or sampling, generally sterilized through electromagnetic waves or irradiation, and however the electromagnetic waves or irradiation may affect the detection circuit board in the detector, leading to a fault occurred to the detection circuit board during sterilization.

SUMMARY

Embodiments of the present disclosure provide a detector and a sterilization system, to address or ease one or more technical issues in the prior art.

As one aspect of embodiments of the present disclosure, embodiments of the present disclosure provide a detector, and the detector includes a housing assembly, a detection assembly and a shielding assembly.

The detection assembly includes a first housing, a detection circuit board and a probe, the detection circuit board is disposed in the first housing and electrically connected with the probe, the detection circuit board includes a sensitive element, and a first end of the probe is fixed in the first housing while a second end stretches out of the first housing; the housing assembly includes a collision housing and a pressing portion that are capable of sliding in relative to each other, the detection assembly is located below a bottom of the pressing portion, the collision housing is used for abutting against a sampling part, and the pressing portion is used for driving the detection assembly to move towards the sampling part, so as to pierce the probe into the sampling part for detection; and when the detector is sterilized through an irradiation ray, the shielding assembly is used for blocking part of the irradiation ray, to form a total-shadow shielding zone for protecting the sensitive element, and at least part of the total-shadow shielding zone is configured as a sealing area for preventing an external object from entering.

Optionally, the first housing includes a bearing shell and a cover body, the bearing shell is hermetically connected with the cover body and forms a sealed storage cavity, the detection circuit board is located in the storage cavity, and the sealing area includes the storage cavity.

Optionally, the first housing further includes a sealing element, the bearing shell is hermetically connected with the cover body through the sealing element, the bearing shell includes a bearing plate and a side wall structure connected with the bearing plate, the side wall structure is provided with a sealing slot, at least part of the sealing element is located in the sealing slot, the cover body includes a main cover body and a raised structure that is connected with the main cover body and extends towards one side of the bearing plate, the raised structure is used for resisting and connecting the sealing element, and the sealing element includes a sealant, a sealing rubber ring or a combination of the sealant and the sealing rubber ring.

Optionally, the shielding assembly is disposed on the detection circuit board, the shielding assembly and the sensitive element are arranged on a path that an irradiation source for sterilization is emitted to the detector, such that the shielding assembly blocks a radiation of the irradiation source to be emitted to the sensitive element, and an irradiation direction of the radiation is different from a pressing direction of the pressing portion.

Optionally, the detection circuit board further includes a battery module or an electronic device, the battery module or the electronic device, the shielding assembly and the sensitive element are all disposed on the detection circuit board, the shielding assembly and the sensitive element are arranged on the path that the irradiation source for sterilization is emitted to the detector, such that the battery module or the electronic device and the shielding assembly block the radiation of the irradiation source to be emitted to the sensitive element together.

Optionally, the irradiation direction of the radiation is perpendicular to the pressing direction of the pressing portion.

Optionally, the probe is brought into the sampling part through a guide needle; the collision housing includes a first barrel-shaped bracket; the pressing portion includes a pressing shell, a second barrel-shaped bracket, a support bracket and an elastic element; the first barrel-shaped bracket is slidingly and partially located in the pressing shell, and an inner wall of the first barrel-shaped bracket is provided with a raised portion; the second barrel-shaped bracket is slidingly sleeved in the first barrel-shaped bracket, the second barrel-shaped bracket includes a barrel-shaped structure and a base plate at a bottom thereof, the barrel-shaped structure is provided with a guide hole along an axial direction, a positioning hole is provided on a path of the guide hole, a plurality of connecting portions extend on an outer edge of the base plate, and the plurality of connecting portions are fixedly connected with the pressing shell; the support bracket is located in the barrel-shaped structure, an elastic resisting portion extends outside the support bracket, and the guide needle is connected with the support bracket; the elastic element is compressed between the base plate and a top of the support bracket; in an initial state, the elastic element is located in a compressed state, and the elastic resisting portion is located in the positioning hole; and under the action of an external force, the pressing shell drives the second barrel-shaped bracket to move in relative to the first barrel-shaped bracket, such that the raised portion moves along the guide hole; when the second barrel-shaped bracket moves to a first preset position in relative to the first barrel-shaped bracket, the guide needle guides the probe to be pierced into the sampling part; and when the second barrel-shaped bracket moves to a second preset position in relative to the first barrel-shaped bracket, the raised portion extrudes the elastic resisting portion out of the positioning hole, the elastic element is released, and the support bracket drives the guide needle to leave the sampling part.

Optionally, the first housing has a cut-through hole, one end of the probe is located in the cut-through hole and stretches into the first housing by passing through a connector of a hole wall of the cut-through hole to be electrically connected with the detection circuit board, the other end of the probe stretches out of the cut-through hole and extends towards a direction away from the pressing portion, the guide needle includes a connecting rod and a needle body connected with the connecting rod, the connecting rod is connected with the support bracket, and the needle body is provided with a through hole that accommodates the probe and is slidingly connected with the probe.

Optionally, the shielding assembly includes a shielding block fixed structure and a shielding block; the shielding block fixed structure is fixed to the collision shell or the pressing portion, and a shielding block accommodating slot is provided on the shielding block fixed structure; and the shielding block is removably accommodated in the shielding block accommodating slot, to block the irradiation ray and form the total-shadow shielding zone located in a designated area.

Optionally, the detector further includes a sealing shell, the sealing shell and an outer wall of the first housing form a first sealing cavity, and the total-shadow shielding zone includes an area in which at least part of the first sealing cavity is located.

Optionally, the detector further includes a sealing structure, the sealing structure is located on one side of the shielding assembly that is away from the first sealing cavity, the sealing structure has a second sealing cavity, and the total-shadow shielding zone includes an area in which at least part of the second sealing cavity is located.

Optionally, the detector further includes a packaging assembly, the packaging assembly includes a first outer shell and a second outer shell, and the first outer shell is mutually coupled with the second outer shell to wrap the housing assembly; the sealing structure includes a first bracket and a second bracket, the first bracket is fixed to the first housing, and the second bracket is fixed to the second outer shell; and in a case that the first outer shell is coupled with the second outer shell, the first bracket cooperates with the second bracket to form the second sealing cavity.

Optionally, the first bracket is a hollow cylinder, and one end of the first bracket is hermetically connected with the first housing while the other end is provided with a fitting groove; the second bracket is a hollow cylinder, and one end of the second bracket that is away from the first bracket is fixedly connected with the second outer shell; and in a case that the first outer shell is coupled with the second outer shell, one end of the second bracket that is away from the second outer shell is embedded into the fitting groove, to form the second sealing cavity together with the first bracket.

Optionally, the detector further includes a shielding block placement structure, and the shielding block placement structure is used for placing the shielding block removably; and in a case that the shielding block is placed on the shielding block placement structure, the shielding block is used for preventing the irradiation ray from being emitted to the sensitive element.

Optionally, a penetrating hole is provided on an end face of the first outer shell; an end face of the second outer shell depresses inward to form a first depressed portion; correspondingly, an end face of the housing assembly that is close to the first outer shell depresses inward to form a second depressed portion; and the penetrating hole, first depressed portion and second depressed portion are disposed correspondingly and combined to form the shielding block placement structure.

Optionally, a first raised shell is provided on the first outer shell, a second raised shell is provided on the second outer shell, the first raised shell cooperates with the second raised shell to form a raised cavity, and the raised cavity is used for accommodating the sensitive element of the detection circuit board in the first housing; an outer wall of the first raised shell and an outer wall of the second raised shell are used for forming the shielding block placement structure.

Optionally, a waist portion of the packaging assembly depresses inward to form a third depressed portion, and the third depressed portion is disposed correspondingly to the first housing; and the third depressed portion is used for forming the shielding block placement structure.

Optionally, a waist portion of the packaging assembly depresses inward to form an annular groove, the annular groove is disposed correspondingly to the first housing; and the annular groove is used for forming the shielding block placement structure.

Optionally, the detection assembly further includes a shielding sheet, the shielding sheet is disposed in the first housing, the shielding sheet is located on a path that the irradiation ray is emitted to the sensitive element, and forms the total-shadow shielding zone for protecting the sensitive element.

Optionally, the detector further includes the packaging assembly, the packaging assembly includes the first outer shell and the second outer shell, and the first outer shell is mutually coupled with the second outer shell to wrap the housing assembly; the detector further includes the sealing structure, and the sealing structure is located on one side of the first housing that is away from the shielding assembly; the sealing structure is provided with the second sealing cavity, the second sealing cavity is used for wrapping at least part of the total-shadow shielding zone, the sealing structure includes the first bracket and the second bracket, the first bracket is fixed to the first housing, and the second bracket is fixed to the second outer shell; the sealing structure further includes an isolating plate, the isolating plate is disposed in the second bracket, and the isolating plate is hermetically connected with the inner wall of the second bracket; a via hole is provided on the second outer shell, and the via hole is disposed correspondingly to the second bracket; and the second bracket and the isolating plate form the shielding block placement structure, and in a case that the shielding block is placed in the shielding block placement structure, the shielding block forms the total-shadow shielding zone for protecting the sensitive element.

As another aspect of embodiments of the present disclosure, embodiments of the present disclosure provide a sterilization system, wherein the sterilization system includes a bearing frame, and the bearing frame is used for cooperating with an irradiation source for sterilization; the bearing frame is located on one side of the irradiation source, one side of the bearing frame that faces the irradiation source is provided with a plurality of bearing portions, and each bearing portion is used for placing one detector described above; and when the detector is placed on the bearing portions, the bearing portions are used for correcting an orientation of the detector, such that the shielding assembly in the detector is located on the path that the irradiation source is emitted to the detector.

Optionally, a center of the bearing frame is disposed correspondingly to the irradiation source; the bearing portions are bearing slots disposed in the bearing frame, the bearing slots in the middle of the bearing frame are disposed perpendicularly, and other bearing slots adjacent to the middle bearing slots tilt towards one side of the irradiation source; and the farther the bearing slots are from the irradiation source, the greater a tilt angle thereof is.

Optionally, the sterilization system further includes at least one fastener of a magnetic suction fastener and a clip fastener, the fastener is used for fixing the detector on the bearing frame, and the bearing portions are also provided with a plurality of first cooling holes; the sterilization system further includes a cover plate, and the cover plate is used for covering one side where the detector is located to fix the detector in cooperation with the bearing portions; and the cover plate has a counterpoint slot for accommodating at least part of the detector, and a plurality of second cooling holes.

Optionally, the bearing portions are also provided with counterpoint structures that are used in cooperation with the detector or another counterpoint structure on the outer package of the detector, such that the detector is capable of being set according to a preset orientation; and when the outer package of the detector has the another counterpoint structure, the detector has a first counterpoint structure, and the outer package has a second counterpoint structure used in cooperation with the first counterpoint structure, such that the detector is set in the outer package according to the preset orientation.

When the embodiments of the present disclosure adopt the above-mentioned technical solution to irradiate the detector for sterilization, the irradiation ray is emitted to a sensitive element on the detection circuit board from one side of the first housing, and the shielding assembly can block the irradiation ray emitted to the sensitive element and form a total-shadow shielding zone not affected by the irradiation ray; and adjusting the position and size of the shielding assembly enables the total-shadow shielding zone formed by the shielding assembly to cover the sensitive element, and weakens or eliminates the irradiation influence on the sensitive element by the irradiation ray, thus relieving a situation that the detection circuit board cannot work normally due to a failure of the sensitive element affected by the irradiation. That is, the present disclosure can also protect the detection circuit board from being damaged in a case of guaranteeing the irradiation ray to sterilize the detector. At the same time, at least part of the total-shadow shielding zone is configured as a sealing area for preventing an external object from entering, which can effectively reduce a pollution situation possibly generated due to not sterilizing the total-shadow shielding zone, to ensure the safety and accuracy of detection.

The above summary is merely for the purpose of specification, and not intended to make a limitation in any way. In addition to the schematic aspects, implementation modes and features described above, the further aspects, implementation modes and features of the present disclosure will be easily understood with reference to drawings and the detailed description below.

BRIEF DESCRIPTION OF THE DRAWINGS

In the drawings, unless otherwise specified, the same drawing signs penetrating through a plurality of drawings indicate the same or similar parts or elements. These drawings are not necessarily drawn to scale. It should be understood that these drawings only describe some implementation modes of the present disclosure, and should not be regarded as limiting the scope of the present disclosure.

REFERENCE SIGNS

Figure 1:
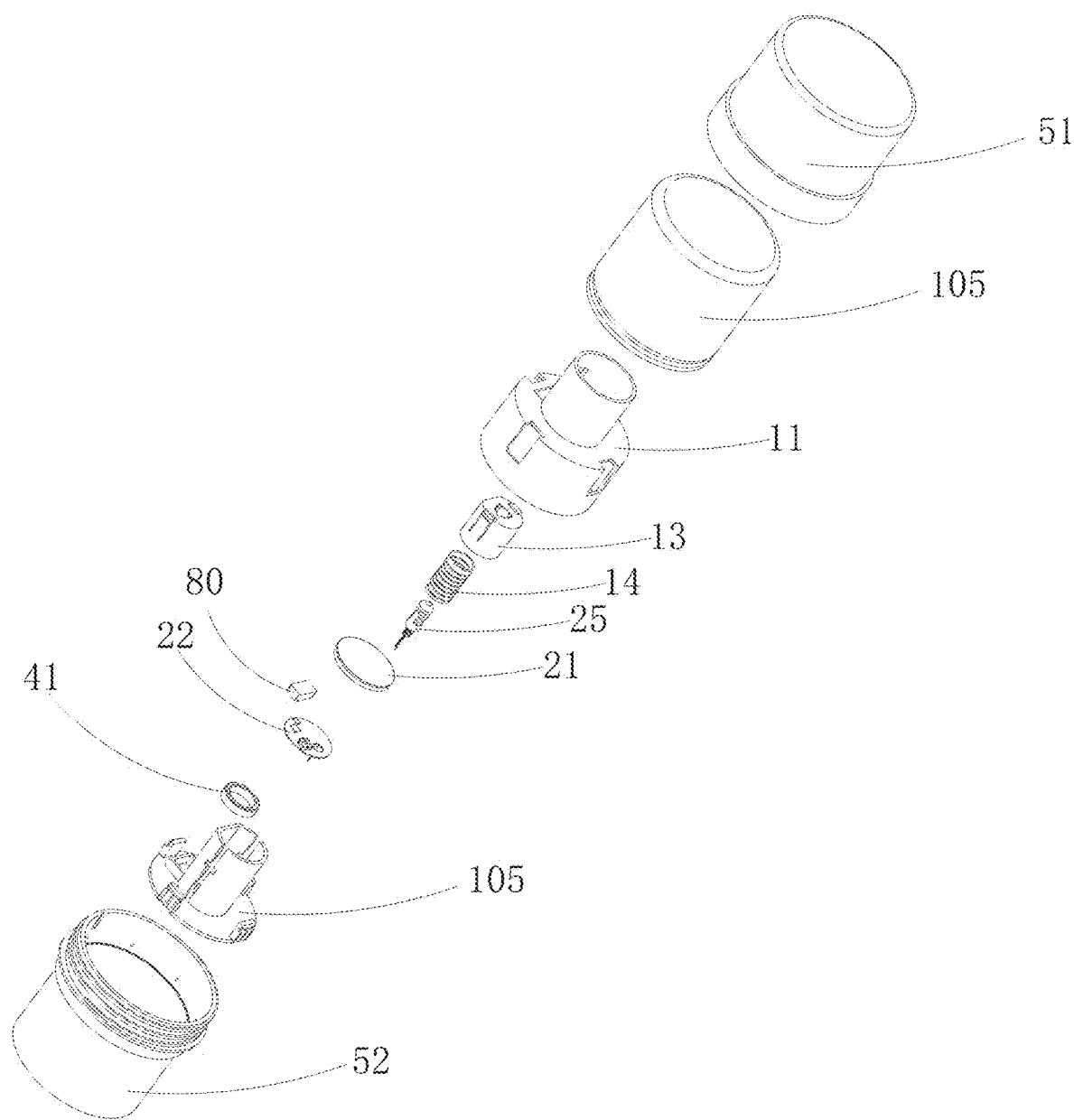
FIG. 1 is an exploded view of a detector according to a first embodiment of the present disclosure.
Figure 2:
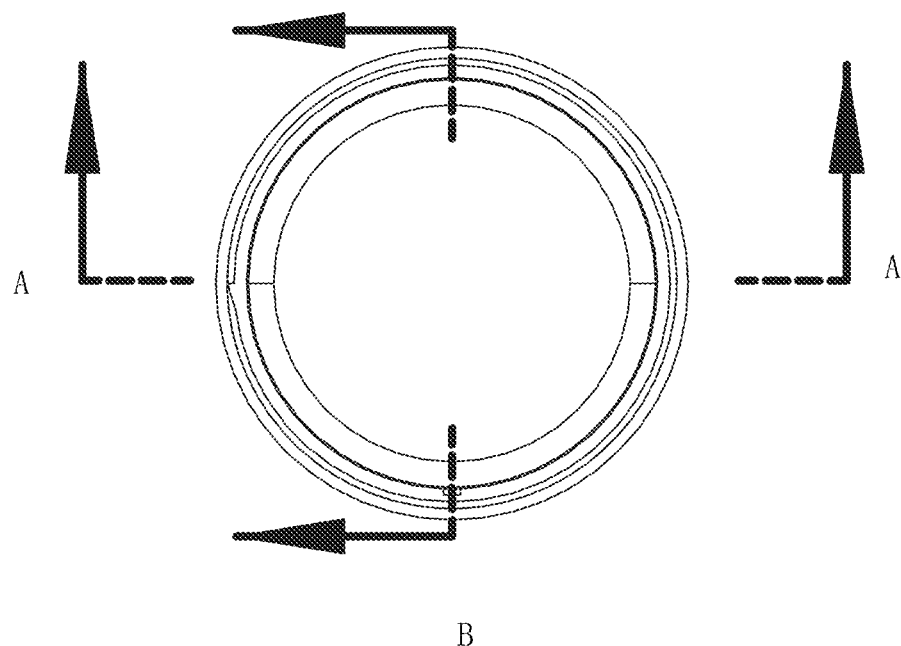
FIG. 2 is a top view of a detector according to embodiments of the present disclosure.
Figure 3:
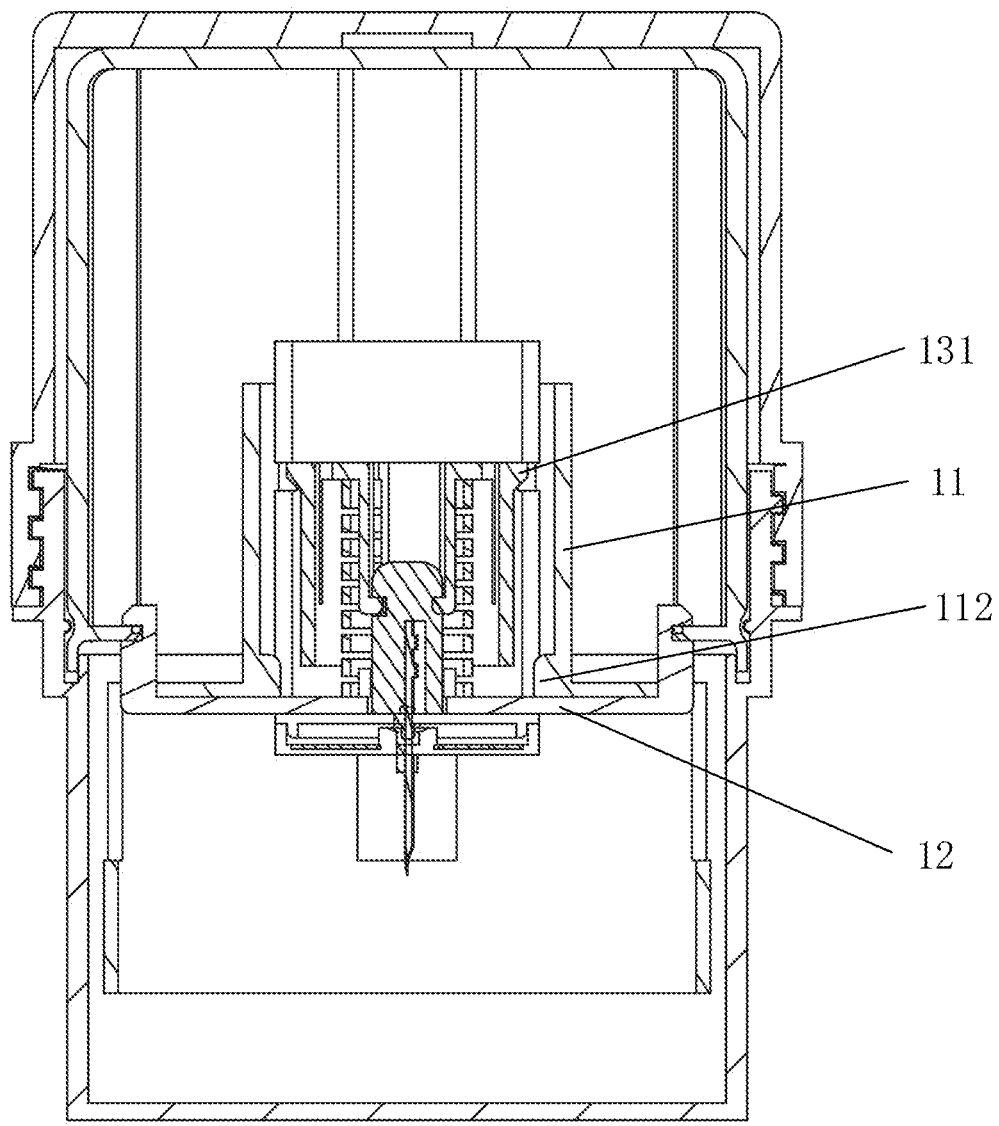
FIG. 3 is a profile diagram along A-A in FIG. 2.
Figure 4:
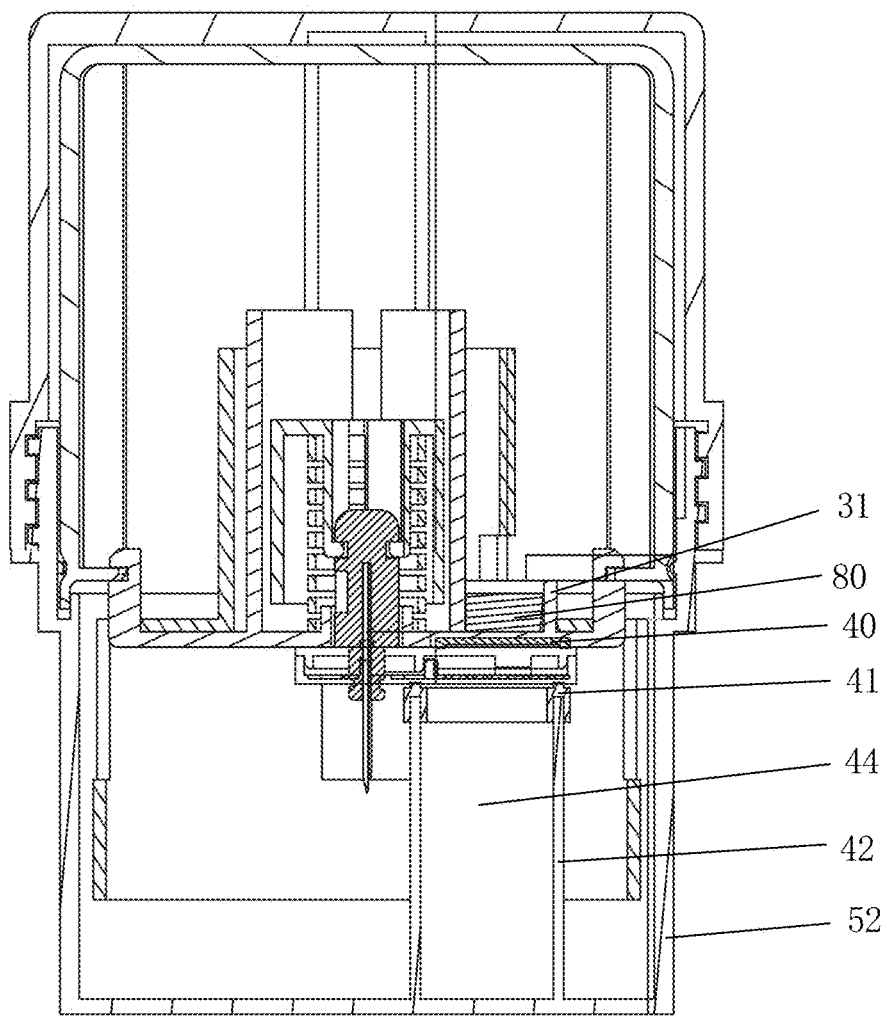
FIG. 4 is a profile diagram along B-B in FIG. 2.
Figure 5:
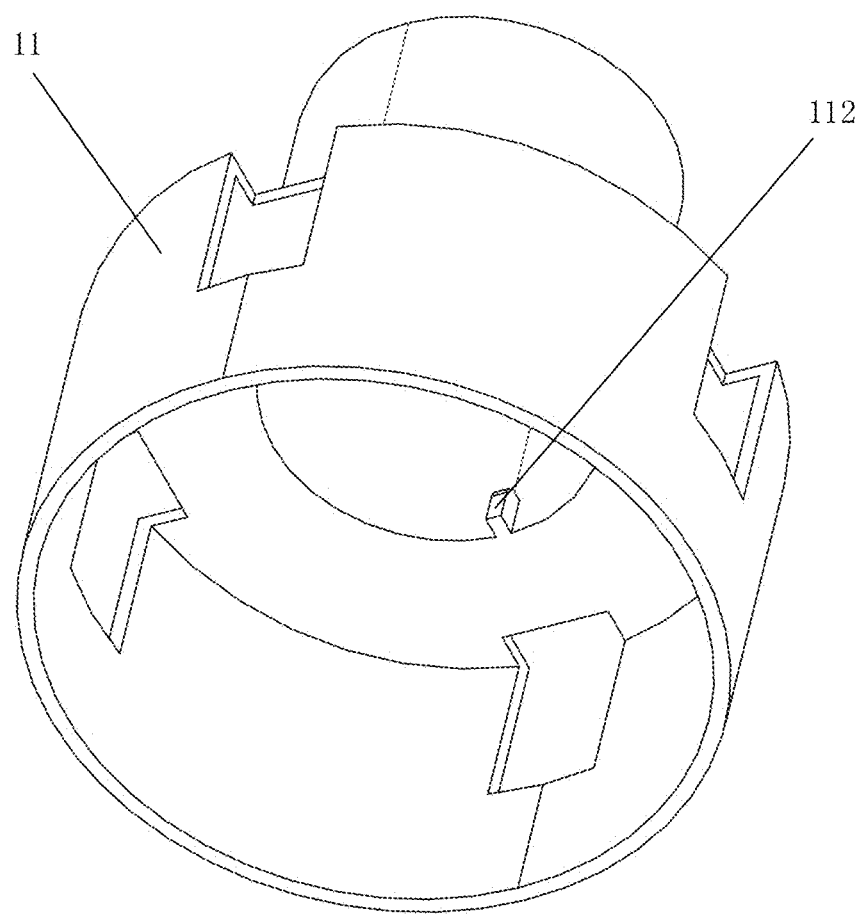
FIG. 5 is a structural schematic diagram of a first barrel-shaped bracket of a detector according to embodiments of the present disclosure.
Figure 6:
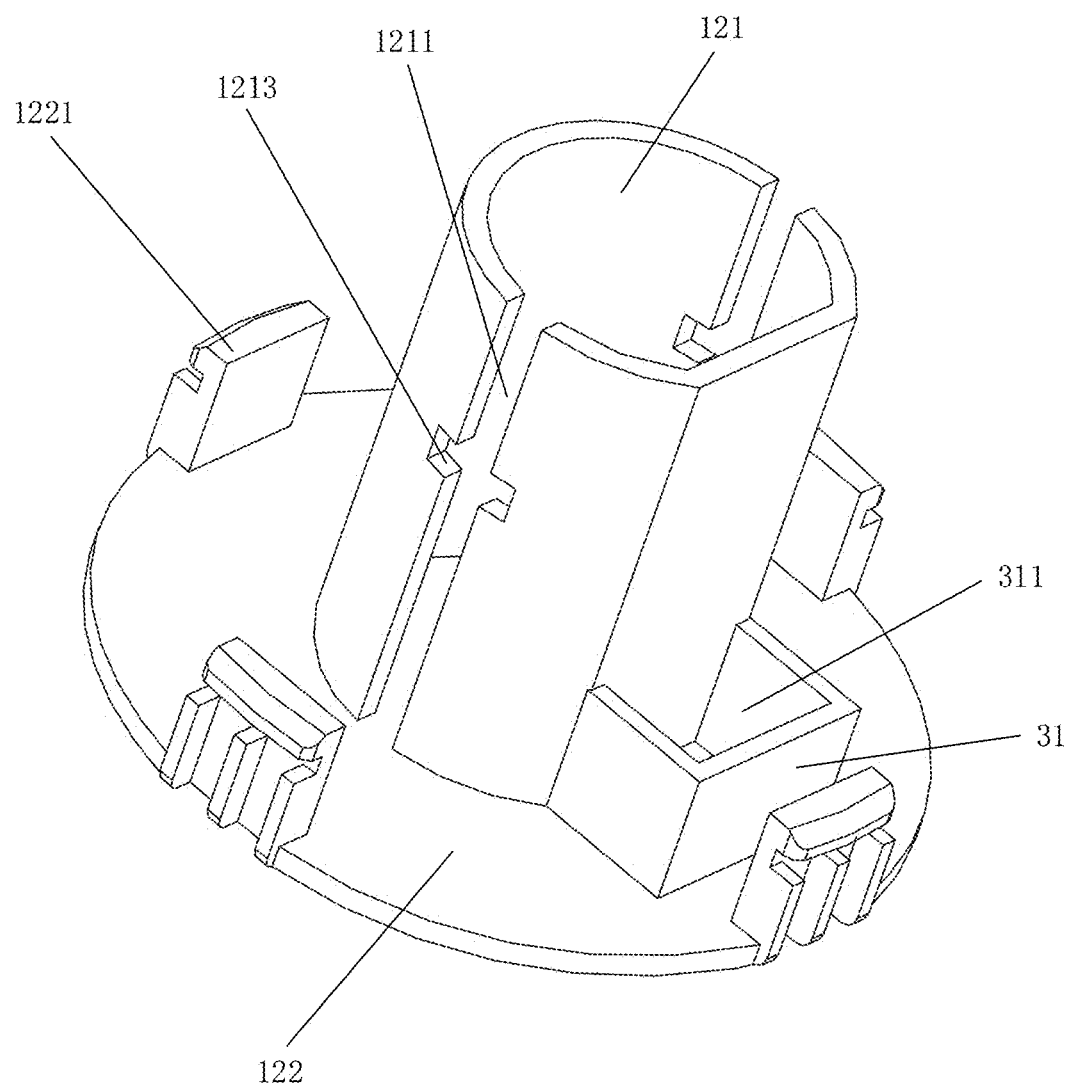
FIG. 6 is a structural schematic diagram of a second barrel-shaped bracket of a detector according to embodiments of the present disclosure.

11. First barrel-shaped bracket; 12. Second barrel-shaped bracket; 13. Support bracket; 14. Elastic element; 17. Shock absorbing assembly; 105. Pressing shell; 12. Raised portion; 121. Barrel-shaped structure; 122. Base plate; 131. Elastic resisting portion; 1211. Guide hole; 1213. Positioning hole; 1221. Connecting portion; 15. Guide needle; 151. Connecting rod; 152. Needle body; 161. Probe; 162. Detection circuit board; 163. Connector;

21. First housing; 22. Detection circuit board; 25. Guide needle; 221. Sensitive element; 227. Fixed hole; 222. Battery module; 211. Bearing shell; 212. Cover body; 213. Sealing element; 2111. Bearing plate; 2112. Side wall structure; 2113. Sealing slot;

31. Shielding block fixed structure; 311. Shielding block accommodating slot;

40. Sealing shell; 41. First bracket; 42. Second bracket; 44. Second sealing cavity; 45. Isolating plate; 411. Fitting groove;

51. First outer shell; 52. Second outer shell; 54. Third depressed portion; 55. Annular groove; 56. Second counterpoint structure; 511. First raised shell; 522. Second raised shell;

61. Main housing; 62. Easy-to-tear film; 63. First counterpoint structure; 64. Third counterpoint structure; 611. End face;

71. Connecting plate; 72. Side baffle; 73. Vertical plate;

80. Shielding block; 801. Total-shadow shielding zone; 80a. Shielding block;

91. Bearing frame; 98. Irradiation source; 92. Fixed element; 93. Cover plate; 94. Fourth counterpoint structure; 911. First cooling hole; 931. Counterpoint slot; 932. Second cooling hole;

T. Path; D1. Radiation direction; D2. Pressing direction.

DETAILED DESCRIPTION OF THE EMBODIMENTS

Only some exemplary embodiments are simply described below. Just as those skilled in the art may understand, the described embodiments may be modified by various different modes without departing from the spirit or scope of the present disclosure. Therefore, drawings and description are regarded as being essentially exemplary, instead of being restrictive.

Please refer to FIGS. 1-24, embodiments of the present disclosure provide a detector, and the detector includes a housing assembly, a detection assembly and a shielding assembly, and detailed descriptions are made below.

The detection assembly includes a first housing 21, a detection circuit board 22 and a probe (not shown in the drawings), the detection circuit board 22 is disposed in the first housing 21 and electrically connected with a first end of the probe, the detection circuit board 22 includes a sensitive element 221, and the first end of the probe is fixed in the first housing 21 while a second end stretches out of the first housing 21;

the housing assembly includes a collision housing and a pressing portion that can slide in relative to each other, the detection assembly is located below a bottom of the pressing portion, the collision housing is used for abutting against a sampling part, the pressing portion is used for driving the detection assembly to move towards the sampling part, so as to pierce the probe into the sampling part, and a detection signal of the probe is transmitted to the detection circuit board 22; and the shielding assembly is disposed on one side of the first housing 21, when the detector is sterilized through an irradiation ray, the shielding assembly is used for blocking part of the irradiation ray, to form a total-shadow shielding zone 801 for protecting the sensitive element 221. The at least part of the total-shadow shielding zone 801 may be configured as a sealing area for preventing an external object from entering, thus effectively reducing a pollution situation possibly generated due to not sterilizing the total-shadow shielding zone 801, to ensure the safety and accuracy of detection. The external object may be external gas, dust, moisture and the like that may carry bacteria.

The sensitive element 221 is a high-precision electronic component that is easily affected by the irradiation ray and breaks down.

The irradiation ray includes but is not limited to an X-ray, an electronic beam and a gamma ray.

When the irradiation ray is emitted to the sensitive element 221 on the detection circuit board 22 from one side of the first housing 21, and the shielding assembly can block the irradiation ray emitted to the sensitive element 221 and form the total-shadow shielding zone 801 not affected by the irradiation ray; and adjusting the position and size of the shielding assembly enables the total-shadow shielding zone 801 formed by the shielding assembly to cover the sensitive element 221, and weakens or eliminates the irradiation influence on the sensitive element 221 by the irradiation ray, thus relieving a situation that the detection circuit board 22 cannot work normally due to a failure of the sensitive element 221 affected by the irradiation. That is, the present disclosure can also protect the detection circuit board 22 from being damaged in a case of guaranteeing the irradiation ray to sterilize the detector.

In this embodiment, the detector may be disposed below the irradiation source when being sterilized, such that the total-shadow shielding zone 801 formed by the shielding assembly wraps the sensitive element 221.

Specifically, a section of the total-shadow shielding zone 801 formed by the shielding assembly is a triangle or a polygon.

Please refer to FIG. 1 to FIG. 6, in one alternative embodiment, the probe is brought into the sampling part through the guide needle 25;

the collision housing includes a first barrel-shaped bracket 11;

the pressing portion includes a pressing shell 105, a second barrel-shaped bracket 12, a support bracket 13 and an elastic element 14;

the first barrel-shaped bracket 11 is slidingly and partially located in the pressing shell 105, and an inner wall of the first barrel-shaped bracket 11 is provided with a raised portion 112;

the second barrel-shaped bracket 12 is slidingly sleeved in the first barrel-shaped bracket 11, the second barrel-shaped bracket 12 includes a barrel-shaped structure 121 and a base plate 122 at a bottom thereof, the barrel-shaped structure 121 is provided with a guide hole 1211 along an axial direction, a positioning hole 1213 is provided on a path of the guide hole 1211, a plurality of connecting portions 1221 extend on an outer edge of the base plate 122, and the plurality of connecting portions 1221 are fixedly connected with the pressing shell 105;

the support bracket 13 is located in the barrel-shaped structure 121, and an elastic resisting portion 131 extends outside the support bracket 13;

the elastic element 14 is compressed between the base plate 122 and a top of the support bracket 13;

in an initial state, the elastic element 14 is located in a compressed state, and the elastic resisting portion 131 is located in the positioning hole 1213; and under the action of an external force, the pressing shell 105 drives the second barrel-shaped bracket 12 to move in relative to the first barrel-shaped bracket 11, such that the raised portion 112 moves along the guide hole 1211; when the second barrel-shaped bracket 12 moves to a first preset position in relative to the first barrel-shaped bracket 11, the guide needle 25 guides the probe to be pierced into the sampling part; and when the second barrel-shaped bracket 12 moves to a second preset position in relative to the first barrel-shaped bracket 11, the raised portion 112 extrudes the elastic resisting portion 131 out of the positioning hole 1213, the elastic element 14 is released, and the support bracket 13 drives the guide needle 25 to leave the sampling part.

In this embodiment, the elastic element 14 may be a spring. Since the elastic element 14 is compressed between the base plate 122 and the top of the support bracket 13, that is, the elastic element 14 will apply an elastic force to the second barrel-shaped bracket 12 and the support bracket 13 to enable the barrel-shaped bracket 12 to be away from the support bracket 13, but the elastic resisting portion 131 is located in the positioning hole 1213, the elastic force generated by the elastic element 14 will push the elastic resisting portion 131 to abut against the inner wall of the positioning hole 1213, such that the second barrel-shaped bracket 12 and the support bracket 13 are stationary relatively.

Specifically, the detector may be used for detecting a plurality of body index data, and the following embodiments take the detection for blood glucose as an example.

When a user adopts the detector for detecting the blood glucose, the user holds the pressing shell 105 to align with the sampling part, such that one end of the collision shell abuts against a vicinity of the sampling portion, at this time the guide needle 25 is not in contact with the sampling part, and then the pressing shell 105 is pushed to move towards one side closing to the sampling part; since the pressing shell 105 is connected with the second barrel-shaped bracket 12, the support bracket 13 also abuts against the second barrel-shaped bracket 12 through the elastic resisting portion 131, the pressing shell 105 can drive the support bracket 13 and the detection assembly to move towards one side closing to the sampling part when driving the second barrel-shaped bracket 12 to move. In a process that the second barrel-shaped bracket 12 drives the detection assembly to move, the guide needle 25 in the detection assembly approaches to the sampling part gradually until the second barrel-shaped bracket 12 moves to the first preset position, and the guide needle 25 is pierced into the sampling part. The probe is pierced along the guide needle 25, thus sampling through the probe, and the probe transmits the data to the detection circuit board 22 to detect blood glucose indexes.

The user continues to push the pressing shell 105 to move towards one side closing to the sampling part until the second barrel-shaped bracket 12 reaches the second preset position. At this time, the raised portion 112 extrudes the elastic resisting portion 131 out of the positioning hole 1213, the elastic resisting portion 131 does not abut against the hole wall of the positioning hole 1213 any more, the support bracket 13 is not limited by the second barrel-shaped bracket 12 any more, the elastic force generated by the compressed elastic element 14 will push the support bracket 13 towards one side away from the sampling part, thus driving the guide needle 25 leave the sampling part, and quickly pulling out the guide needle 25 from the sampling part. Since the detection assembly is not connected with the support bracket 13, the probe is not pulled out of the sampling part together with the guide needle 25, instead of remaining in the sampling part for continuous sampling detection, thus dynamically feeding back a detection result.

The user may push the pressing shell 105 through the structure of the above-mentioned detector, the probe is pierced into the sampling part through the guide needle 25, the support bracket 13 is not limited by the second barrel-shaped bracket 12 any more after the guide needle 25 brings the probe into the sampling part for a certain depth, the spring is released such that the guide needle 25 is quickly pulled out of the sampling part along the piercing path, so situations of strong pain, skin injury and the like of to-be-detected personnel, caused by deviating from the trajectory, relatively slow needle withdrawal and the like, do not appear easily, thus improving the experience of the to-be-detected personnel.

Further, in this embodiment, the shielding assembly includes a shielding block fixed structure 31 and a shielding block 80;

the shielding block fixed structure 31 is fixed above the base plate 122, and a shielding block accommodating slot 311 is provided on the shielding block fixed structure; 31 and the shielding block 80 is removably accommodated in the shielding block accommodating slot 311, to block the irradiation ray and form the total-shadow shielding zone 801 in a designated area.

It can be understood that after irradiation sterilization for the detector is completed, the shielding block 80 may be taken out of the shielding block accommodating slot 311, and may also be kept in the detector.

Specifically, the shielding block 80 is a cuboid structure. The shielding block 80 has a density greater than 1,000 kg/m$^3$. It can be understood that the greater the density of the shielding block 80, the better the effect that the shielding block 80 blocks the irradiation ray.

It is to be noted that although the shielding block 80 can block the irradiation ray, the sterilization strength to the total-shadow shielding zone 801 by the irradiation ray is also weakened, the insufficient sterilization strength may appear, thus not sterilizing the total-shadow shielding zone 801 completely, leading to bacteria still existing in the total-shadow shielding zone 801 in the detector after the irradiation sterilization, thereby polluting other areas of the detector.

Based on the above-mentioned issues, in this embodiment, the detector further includes a sealing shell 40, the sealing shell 40 is located between the base plate 122 and the first housing 21, the sealing shell 40 and the outer wall of the first housing 21 form a first sealing cavity (not shown in the drawings), and the first sealing cavity is disposed correspondingly to the shielding assembly. It can be understood that the total-shadow shielding zone 801 includes an area where part of the first sealing cavity is located. The sensitive element can be disposed in the first sealing cavity.

Preferably, a cross section of the first sealing cavity is greater than or equal to that of the total-shadow shielding zone formed by the shielding assembly.

A gap exists between the base plate 122 and the first housing 21, while the gap is also located in the total-shadow shielding zone 801, therefore setting the sealing shell 40 between the base plate 122 of the second barrel-shaped bracket 12 and the first housing 21 may wrap a gap therebetween into the first sealing cavity, thus avoiding a situation that residual bacteria possibly exists in the gap therebetween due to the irradiation ray weakened by the shielding block 80, then other areas of the detector are polluted.

Further, in this embodiment, the detector further includes a sealing structure, the sealing structure is located on one side of the shielding assembly that is away from the first sealing cavity, and the sealing structure has a second sealing cavity 44. It can be understood that the total-shadow shielding zone 801 includes the area in which at least part of the second sealing cavity 44 is located, and specifically the second sealing cavity 44 is used for wrapping the at least part of the total-shadow shielding zone 801, that is, the area where the second sealing cavity 44 is located may be equal or or exceed the total-shadow shielding zone 801.

The at least part of the total-shadow shielding zone 801 is wrapped through the second sealing cavity 44, such that the bacteria possibly remaining in the total-shadow shielding zone 801 is isolated from other areas of the detector, thus avoiding the situations that the sterilization strength to the total-shadow shielding zone 801 is insufficient due to the irradiation ray weakened by the shielding block 80, then other areas of the detector are polluted.

Further, the detector further includes a packaging assembly, the packaging assembly includes a first outer shell 51 and a second outer shell 52, and the first outer shell 51 is mutually coupled with the second outer shell 52 to wrap the housing assembly;

the sealing structure includes a first bracket 41 and a second bracket 42, the first bracket 41 is fixed to the first housing 21, and the second bracket 42 is fixed to the second outer shell 52; and in a case that the first outer shell 51 is coupled with the second outer shell 52, the first bracket 41 cooperates with the second bracket 42 to form the second sealing cavity 44.

When the user unpacks the detector for use, the second bracket 42 is removed together with the second outer shell 52 since the second bracket 42 is fixedly connected with the second outer shell 52, thus avoiding the second bracket 42 interfering the use of the user. However, at this time the user has unpacked the detector, the second sealing cavity 44 is opened, but the detector has been in contact with the outside world and used, so there is no problem that the bacteria in the second sealing cavity 44 pollute other areas of the detector.

Figure 7:
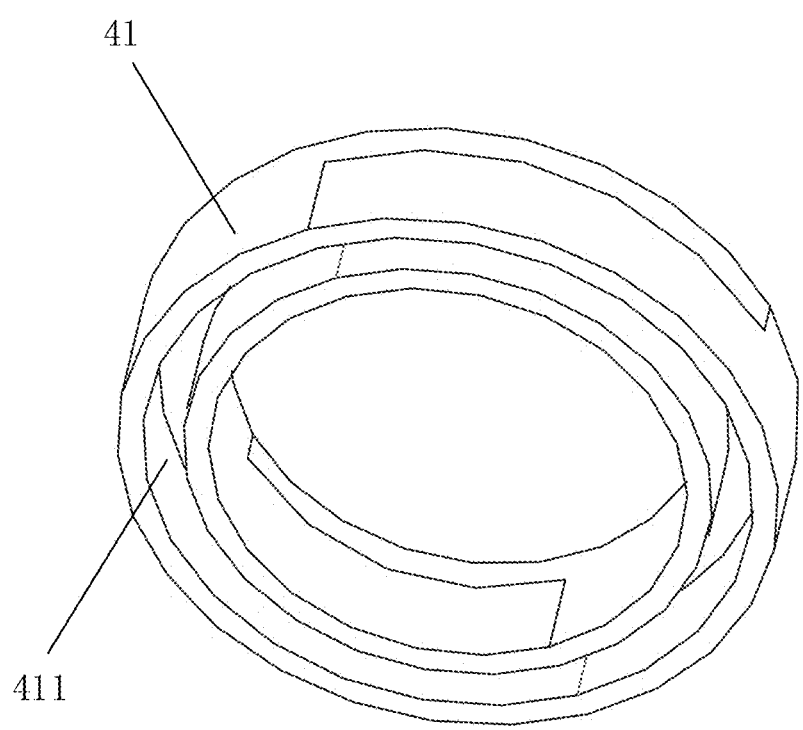
FIG. 7 is a structural schematic diagram of a first bracket of a detector according to embodiments of the present disclosure.
Figure 8:
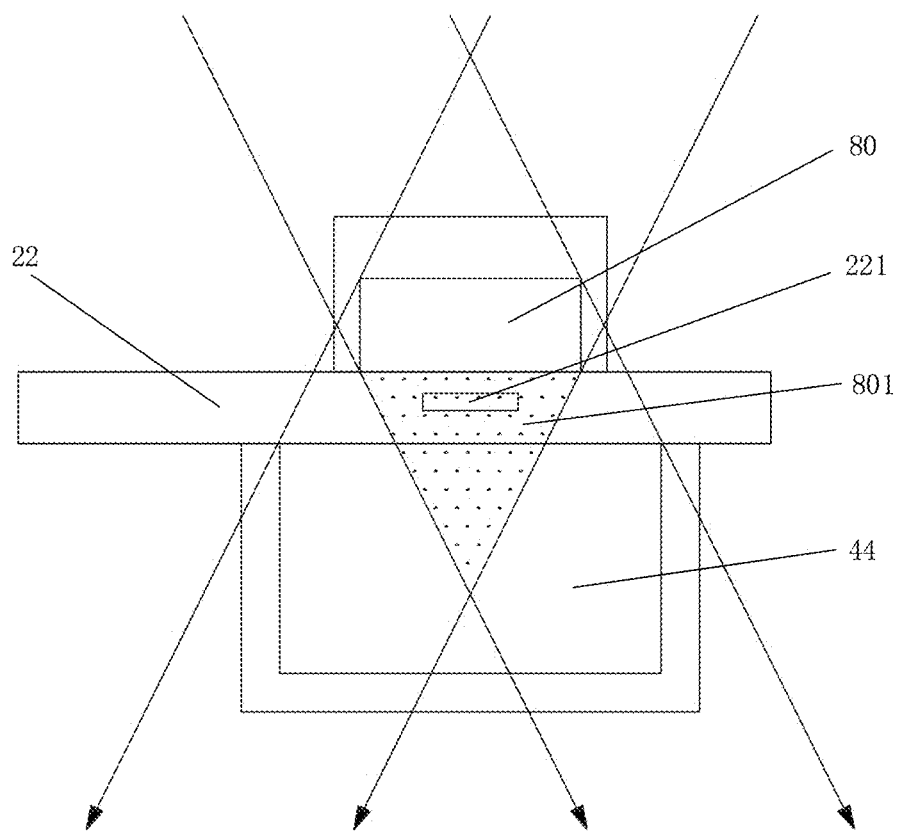
FIG. 8 is a schematic diagram of a total-shadow shielding zone of a detector according to embodiments of the present disclosure.

Further, please combine with FIGS. 1-6 and refer to FIG. 7, the first bracket 41 is a hollow cylinder, and one end of the first bracket 41 is hermetically connected with the first housing 21 while the other end is provided with a fitting groove 411;

the second bracket 42 is a hollow cylinder, and one end of the second bracket 42 that is away from the first bracket 41 is fixedly connected with the second outer shell 52; and in a case that the first outer shell 51 is coupled with the second outer shell 52, one end of the second bracket 42 that is away from the second outer shell 52 is embedded into the fitting groove 411, to form the second sealing cavity 44 together with the first bracket 41.

Specifically, the first bracket 41 may be made of a flexible material, including but not being limited to silica gel, thermoplastic polyurethane (TPU), rubber, plastics, etc. The first bracket 41 made of the flexible material can be hermetically connected with the second bracket 42 more tightly, to ensure the connecting tightness therebetween.

Alternatively, in this embodiment, the first outer shell 51 is in threaded connection with the second outer shell 52.

On the one hand, the threaded connection between the first outer shell 51 and the second outer shell 52 may enable the detector to fit with the packaging assembly more tightly, thus avoiding accidental unpacking caused by shaking during transportation; and on the other hand, in a process that the detector is packed into the packaging assembly, since the second bracket 42 is fixed to the second outer shell 52, a pretightening force can be provided to the bracket when tightening the first outer shell 51 and the second outer shell 52, such that the second bracket 42 is closer to the first bracket 41 and the second bracket 42 fits with the first bracket 41 more tightly, thus ensuring the tightness of the bracket.

Further, the detector further includes a shielding block placement structure, and the shielding block placement structure is used for placing the shielding block 80 removably; and in a case that the shielding block 80 is placed on the shielding block placement structure, the shielding block 80 is used for preventing the irradiation ray from being emitted to the sensitive element 221.

When the detector is sterilized through the irradiation, the shielding block 80 is placed on the shielding block placement structure of the detector, to further protect the sensitive element 221 from being affected by the irradiation.

Figure 9:
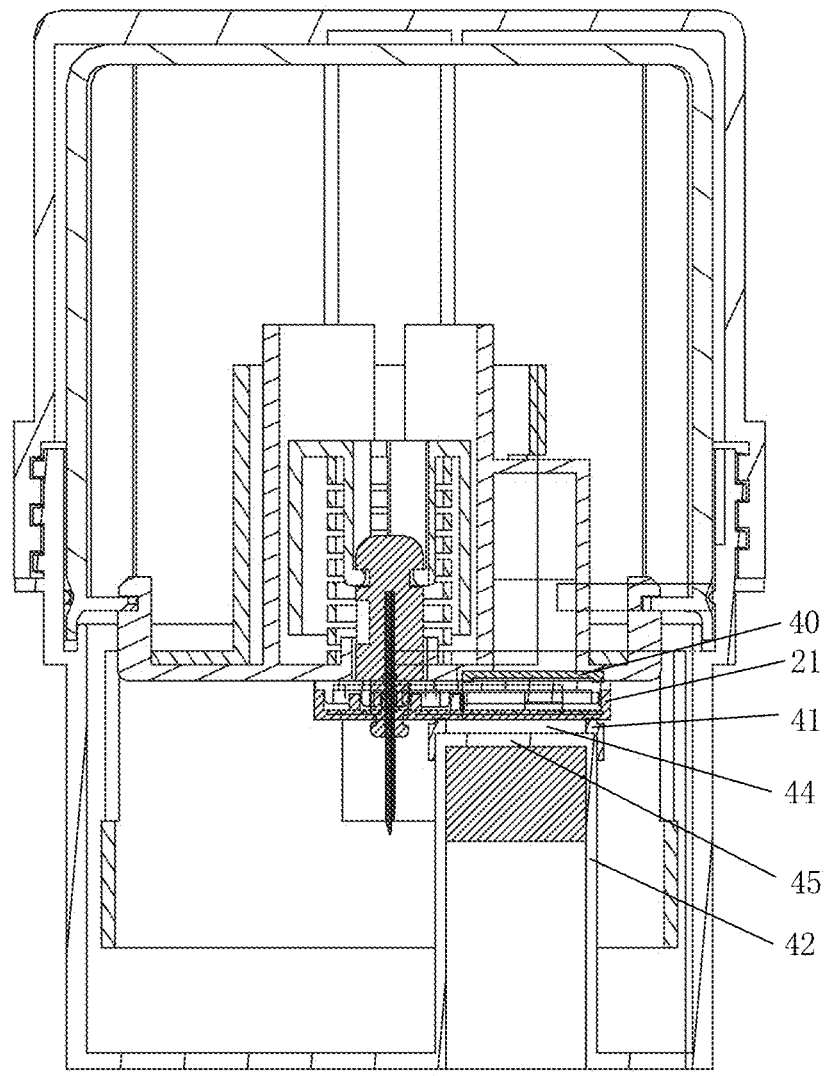
FIG. 9 is a profile diagram of a detector according to a second embodiment of the present disclosure.

In other alternative embodiments, as shown in FIG. 9, the detector further includes a packaging assembly, the packaging assembly includes a first outer shell 51 and a second outer shell 52, and the first outer shell 51 is mutually coupled with the second outer shell 52 to wrap the housing assembly;

the detector further includes a sealing structure, and the sealing structure is located on one side of the first housing 21 that is away from the shielding assembly; and the sealing structure has a second sealing cavity, the second sealing cavity is used for wrapping at least part of the total-shadow shielding zone, the sealing structure includes a first bracket 41 and a second bracket 42, the first bracket 41 is fixed to the first housing 21, and the second bracket 42 is fixed to the second outer shell 52;

the sealing structure further includes an isolating plate 45, the isolating plate 45 is disposed in the second bracket 42, and the isolating plate 45 is hermetically connected with the inner wall of the second bracket 42;

a via hole is provided on the second outer shell 52, and the via hole is disposed correspondingly to the second bracket 42; and the second bracket 42 and the isolating plate 45 form the shielding block placement structure, and in a case that the shielding block 80 is placed in the shielding block placement structure, the shielding block 80 forms the total-shadow shielding zone for wrapping the sensitive element.

The shielding block 80 is placed in the second bracket 42 through the via hole, and the shielding block 80 is enabled to abut against the isolating plate 45 to shield the irradiation ray. The shielding block 80 in the second bracket 42 is disposed in relative to the shielding block 80 in the shielding assembly on the other side of the first housing 21, to block the irradiation rays on both sides of the sensitive element 221, respectively.

After irradiation sterilization, the shielding block 80 can be directly taken out of the second bracket 42 through the via hole, such that the shielding block 80 is mounted in another detector when the another detector is sterilized, to achieve the reuse of the shielding block 80.

In other alternative embodiments, a penetrating hole is provided on an end face of the first outer shell;

an end face of the second outer shell depresses inward to form a first depressed portion;

correspondingly, an end face of the housing assembly that is close to the first outer shell depresses inward to form a second depressed portion; and the penetrating hole, first depressed portion and second depressed portion are disposed correspondingly and combined to form the shielding block placement structure.

When the shielding block is placed on the shielding block placement structure, the shielding block is located on two opposite sides of the sensitive element to form the total-shadow shielding zone for wrapping the sensitive element.

Figure 10:
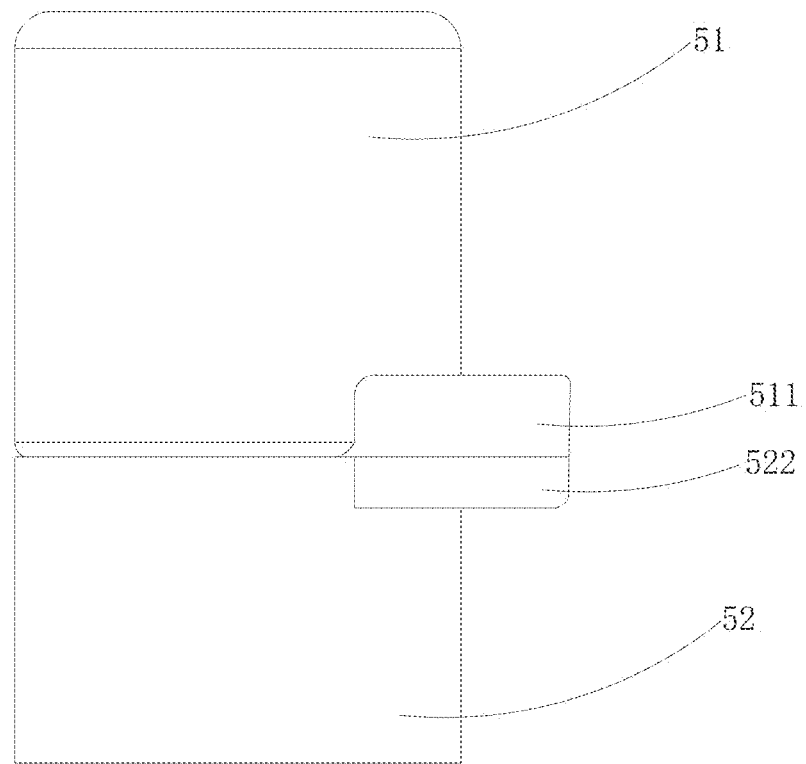
FIG. 10 is a structural schematic diagram of a detector according to a third embodiment of the present disclosure.

In another alternative embodiment, as shown in FIG. 10, a first raised shell 511 is provided on the first outer shell 51, a second raised shell 522 is provided on the second outer shell 52, the first raised shell 511 cooperates with the second raised shell 522 to form a raised cavity (not shown in the drawings), and the raised cavity is used for accommodating the sensitive element 221 of the detection circuit board 22 in the first housing 21;

an outer wall of the first raised shell 511 and an outer wall of the second raised shell 522 are used for forming the shielding block placement structure.

In this embodiment, the corresponding part of the high-precision electronic component in the detection circuit board 22 protrudes from the housing assembly, and the first raised shell 511 and the second raised shell 522 accommodate part of the detection circuit board 22. In this embodiment, the shielding block 80 can be disposed at an upper end of the first raised shell 511 and a lower end of the second raised shell 522, and sides of the first raised shell 511 and the second raised shell 522, such that the shielding block 80 blocks the irradiation ray generated during irradiation sterilization.

Figure 11:
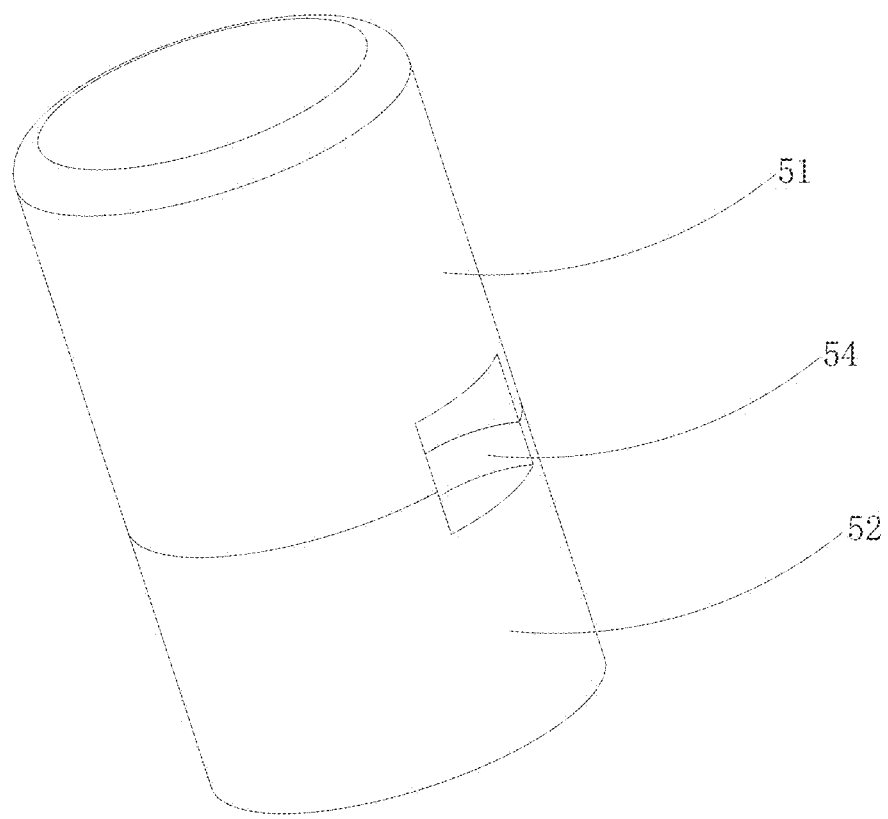
FIG. 11 is a structural schematic diagram of a detector according to a fourth embodiment of the present disclosure.

In another alternative embodiment, as shown in FIG. 11, a waist portion of the packaging assembly depresses inward to form a third depressed portion 54, and the third depressed portion 54 is disposed correspondingly to the first housing 21; and the third depressed portion 54 is used for forming the shielding block placement structure.

The shielding block 80 is disposed on the third depressed portion 54 at the waist portion of the first housing 21, such that the shielding block 80 is located on the path that the irradiation ray is emitted to the sensitive element 221, thus reducing the situation that the sensitive element 221 breaks down caused when the irradiation ray is emitted to the side of the sensitive element 221.

Figure 12:
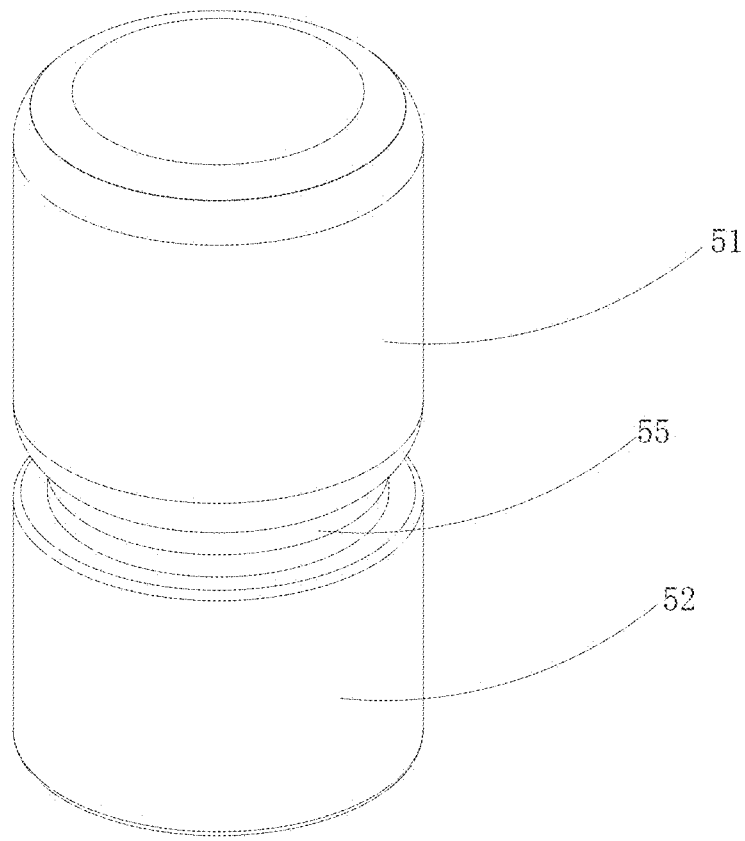
FIG. 12 is a structural schematic diagram of a detector according to a fifth embodiment of the present disclosure.

In another alternative embodiment, as shown in FIG. 12, a waist portion of the packaging assembly depresses inward to form an annular groove 55, the annular groove 55 is disposed correspondingly to the first housing 21; and the annular groove 55 is used for forming the shielding block placement structure.

The shielding block 80 is disposed on the annular groove 55 at the waist portion of the first housing 21, such that the irradiation ray from any side end of the sensitive element 221 can be blocked, the shielding block 80 is located on the path that the irradiation ray is emitted to the sensitive element 221, thus reducing the influence on the sensitive element 221 by the irradiation ray.

In one alternative embodiment, the guide needle 25 is fixedly connected with the support bracket 13, and one end of the guide needle 25 passes through the detection assembly; and the detector further includes a needle sleeve, the needle sleeve is used for accommodating the guide needle 25, and one end of the needle sleeve is hermetically connected with the first housing 21.

Sterilization from the irradiation ray is received throughout the needle sleeve, thus not existing bacteria. The guide needle 25 is accommodated in the needle sleeve, such that the guide needle 25 is isolated from other spaces of the detector, to avoid a situation that the shielding block 80 blocks the irradiation ray, leading to the insufficient sterilization strength and then causing the guide needle 25 to be polluted by the residual bacteria.

In other alternative embodiments, the other end of the needle sleeve is fixedly connected with the second outer shell 52.

In other alternative embodiments, the detector further includes a shielding sheet, the shielding sheet is disposed in the first housing, the shielding sheet is located on a path that the irradiation ray is emitted to the sensitive element, and forms the total-shadow shielding zone for wrapping the sensitive element.

Specifically, the shielding sheet may be located above the sensitive element 221 to form the total-shadow shielding zone to cover the sensitive element 221.

Please combine with FIGS. 1-12 and refer to FIGS. 13-19, embodiments of the present disclosure provide a detector, and the detector includes a housing assembly, a detection assembly and a shielding assembly, where:

the detection assembly includes a first housing 21, a detection circuit board 22 and a probe, the detection circuit board 22 is disposed in the first housing 21 and electrically connected with a first end of the probe, the detection circuit board 22 includes a sensitive element 221, and the first end of the probe is fixed in the first housing 21 while a second end stretches out of the first housing 21;

the housing assembly includes a collision housing and a pressing portion that can slide in relative to each other, the detection assembly is located below a bottom of the pressing portion, the collision housing is used for abutting against a sampling part, the pressing portion is used for driving the detection assembly to move towards the sampling part, so as to pierce the probe into the sampling part, and a detection signal of the probe is transmitted to the detection circuit board 22; and the shielding assembly is disposed in the first housing 21, when the detector is sterilized through an irradiation ray, the shielding assembly is used for blocking part of the irradiation ray, to form a total-shadow shielding zone 801 for protecting the sensitive element 221.

Figure 13:
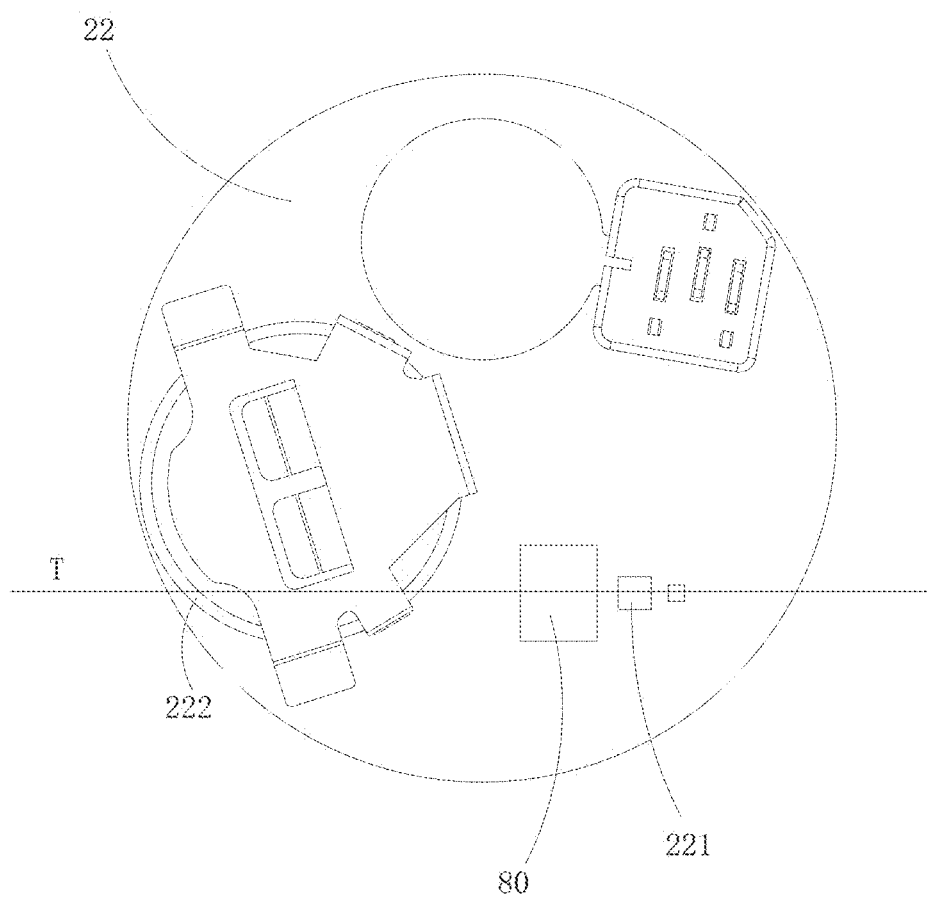
FIG. 13 is a structural schematic diagram of a detection circuit board of a detector according to a sixth embodiment of the present disclosure.

Further, as shown in FIG. 13, the detection circuit board 22 is also provided with a battery module 222, the battery module 222, the shielding assembly 82a and the sensitive element 221 are all disposed on the path that the irradiation source for sterilization is emitted to the detector, such that the battery module 222 and shielding assembly 80a block the radiation of the irradiation source to be emitted to the sensitive element 221 together.

The difference from the above-mentioned embodiment is that the shielding assembly in the detector in this embodiment is disposed in the first housing 21.

When the irradiation ray is emitted to the sensitive element 221 on the detection circuit board 22 from one side of the first housing 21, and the shielding assembly can block the irradiation ray emitted to the sensitive element 221 and form the total-shadow shielding zone 801 not affected by the irradiation ray; and adjusting the position and size of the shielding assembly enables the total-shadow shielding zone 801 formed by the shielding assembly to cover the sensitive element 221, and weakens or eliminates the irradiation influence on the sensitive element 221 by the irradiation ray, thus relieving a situation that the detection circuit board 22 cannot work normally due to a failure of the sensitive element 221 affected by the irradiation. That is, the present disclosure can also protect the detection circuit board 22 from being damaged in a case of guaranteeing the irradiation ray to sterilize the detector.

After being emitted from an accelerator, the electronic beam passes through non-vacuum substances in various parts such as air, sensor outer surface and outer shell; and these substances form a strong scattering action on electron, but the electron cannot penetrate through the shielding assembly, and will form a low-radiation area below the shielding assembly, that is, the total-shadow shielding zone. Due to different electronic scattering angles, an edge of the total-shadow shielding zone also has a radiation dosage, and the radiation dosage in the area from the edge of the total-shadow shielding zone to the center and the upper part closing to the shielding assembly is relatively small, and the dosage further away from the shielding assembly is relatively great. By adjusting the structure and position of the shielding assembly, the area with the relatively small radiation dosage in the total-shadow shielding zone formed by the shielding assembly wraps the sensitive element.

Further, the probe is brought into the sampling part through the guide needle 25;

the collision housing includes a first barrel-shaped bracket 11;

the pressing portion includes a pressing shell 105, a second barrel-shaped bracket 12, a support bracket 13 and an elastic element 14;

the first barrel-shaped bracket 11 is slidingly and partially located in the pressing shell 105, and an inner wall of the first barrel-shaped bracket 11 is provided with a raised portion 112;

the second barrel-shaped bracket 12 is slidingly sleeved in the first barrel-shaped bracket 11, the second barrel-shaped bracket 12 includes a barrel-shaped structure 121 and a base plate 122 at a bottom thereof, the barrel-shaped structure 121 is provided with a guide hole 1211 along an axial direction, a positioning hole 1213 is provided on a path of the guide hole 1211, a plurality of connecting portions 1221 extend on an outer edge of the base plate 122, and the plurality of connecting portions 1221 are fixedly connected with the pressing shell 105;

the support bracket 13 is located in the barrel-shaped structure 121, and an elastic resisting portion 131 extends outside the support bracket 13;

the elastic element 14 is compressed between the base plate 122 and a top of the support bracket 13;

in an initial state, the elastic element 14 is located in a compressed state, and the elastic resisting portion 131 is located in the positioning hole 1213; and under the action of an external force, the pressing shell 105 drives the second barrel-shaped bracket 12 to move in relative to the first barrel-shaped bracket 11, such that the raised portion 112 moves along the guide hole 1211; when the second barrel-shaped bracket 12 moves to a first preset position in relative to the first barrel-shaped bracket 11, the guide needle 25 guides the probe to be pierced into the sampling part; and when the second barrel-shaped bracket 12 moves to a second preset position in relative to the first barrel-shaped bracket 11, the raised portion 112 extrudes the elastic resisting portion 131 out of the positioning hole 1213, the elastic element 14 is released, and the support bracket 13 drives the guide needle 25 to leave the sampling part.

Figure 14:
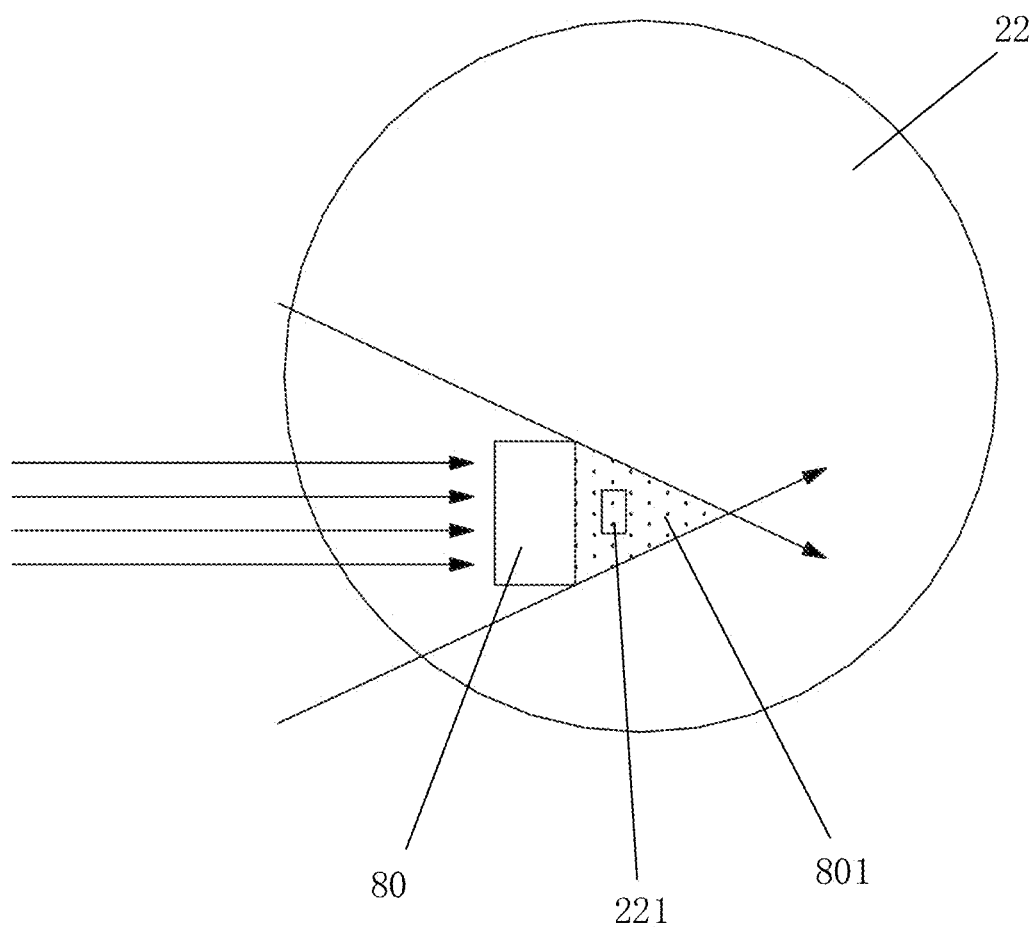
FIG. 14 is a structural schematic diagram of a total-shadow shielding zone formed by a shielding frame in FIG. 13.

In one alternative embodiment, as shown in FIG. 13 and FIG. 14, the shielding assembly includes a shielding frame, the shielding frame is fixed to one side of the detection circuit board 22 that is provided with the sensitive element 221, and the shielding frame is used for blocking the irradiation ray to form the total-shadow shielding zone 801 in the designated area.

When being sterilized, the detector can be transversely placed, the position of the detector is adjusted such that the shielding frame is located on the path that the irradiation ray is emitted to the sensitive element 221, and the total-shadow shielding zone 801 formed by the shielding frame protects the sensitive element 221 from being affected by the irradiation ray.

Figure 15:
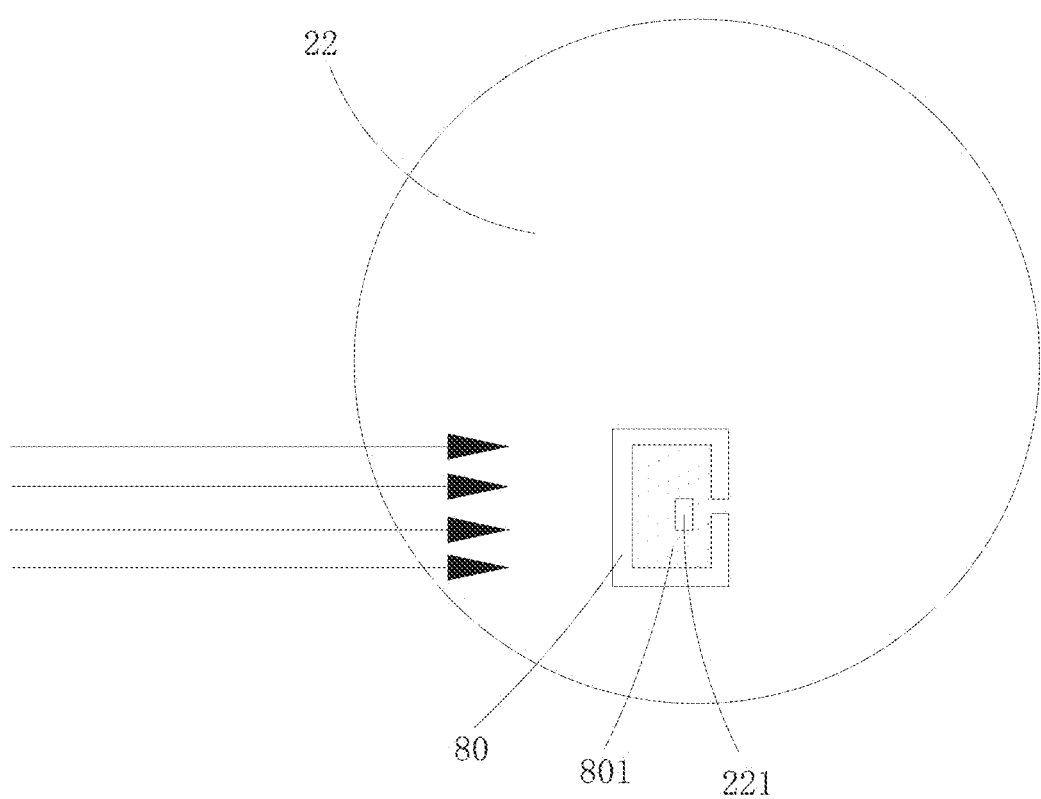
FIG. 15 is a structural schematic diagram of a total-shadow shielding zone formed by a shielding frame of a detector according to a seventh embodiment of the present disclosure.

In one alternative embodiment, as shown in FIG. 15, the shielding assembly includes a shielding frame, the shielding frame is fixed to the detection circuit board 22 and disposed around a periphery of the sensitive element 221, and the shielding frame is used for blocking the irradiation ray to form the total-shadow shielding zone 801 in the designed area.

When being sterilized, the detector can be transversely placed, since the shielding frame is disposed around the periphery of the sensitive element 221, the space in the shielding frame is all the total-shadow shielding zone 801, which can block the irradiation ray emitted from any direction of the side end of the sensitive element 221, to protect the sensitive element 221 from being affected by the irradiation ray.

Figure 16:
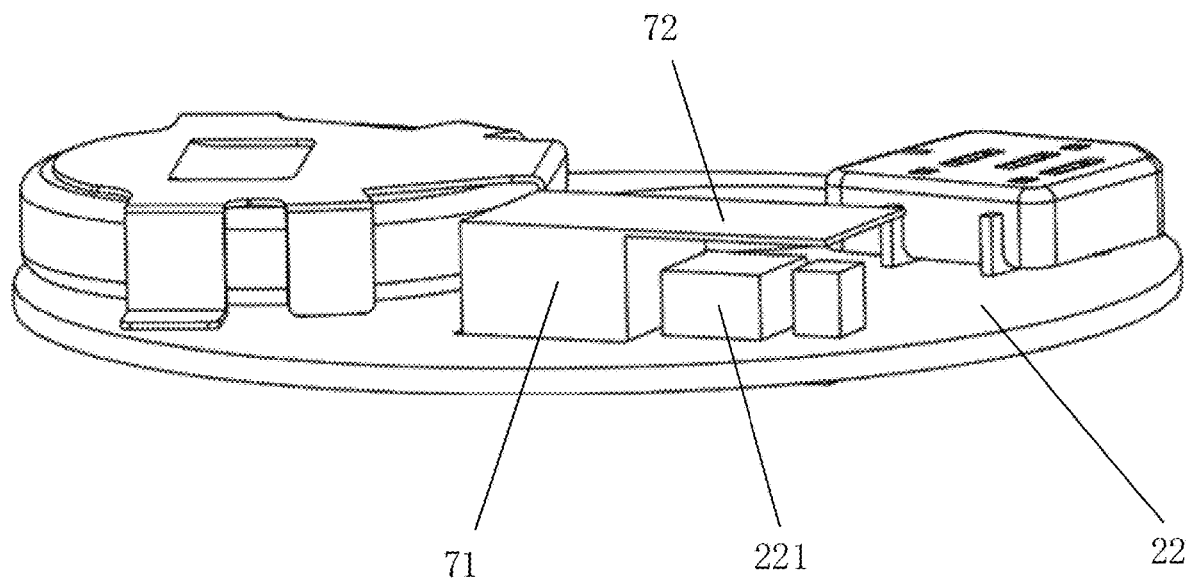
FIG. 16 is a structural schematic diagram of a detection circuit board of a detector according to an eighth embodiment of the present disclosure.
Figure 17:
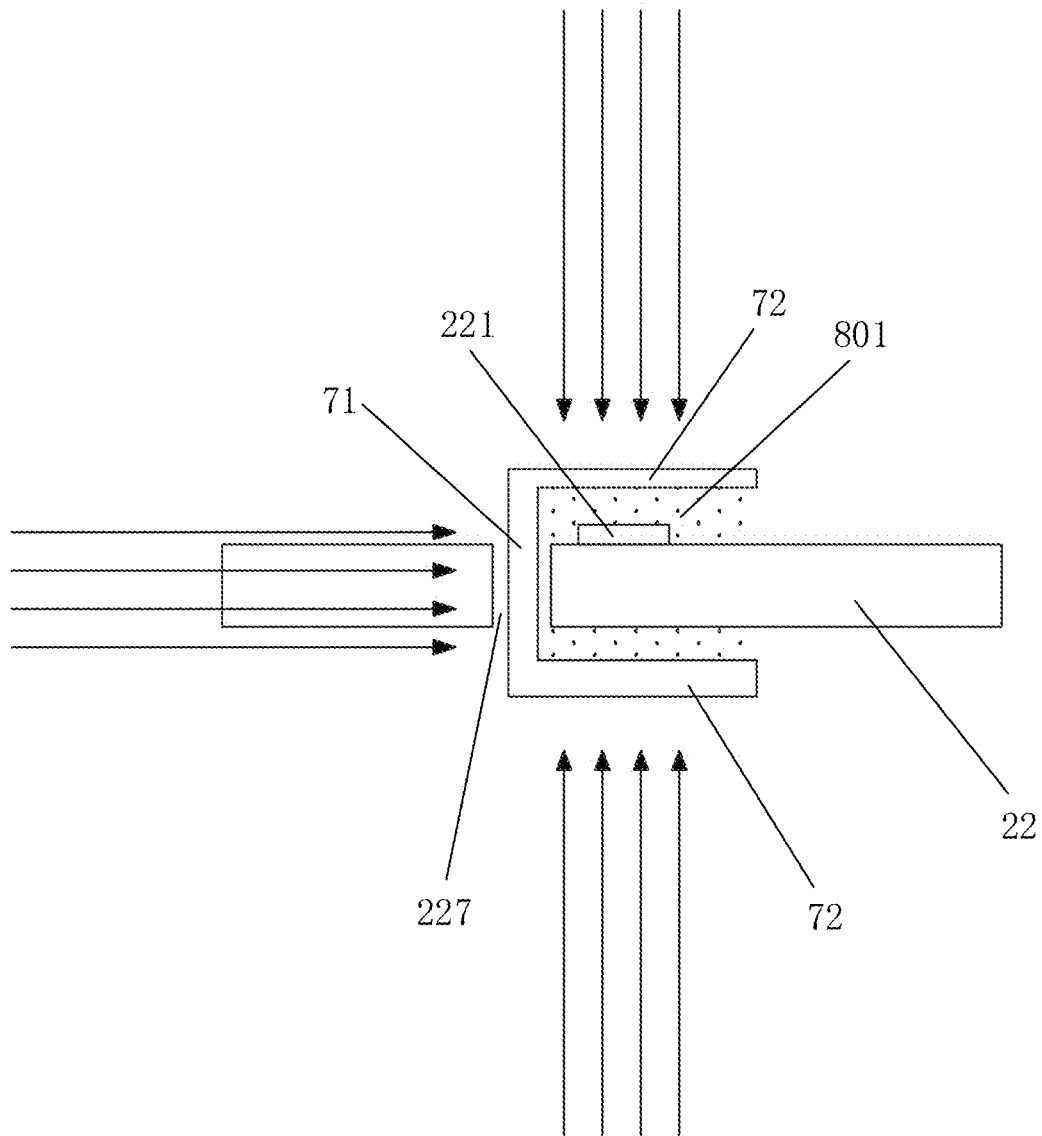
FIG. 17 is a structural schematic diagram of a total-shadow shielding zone formed by a shielding frame in FIG. 16.
Figure 18:
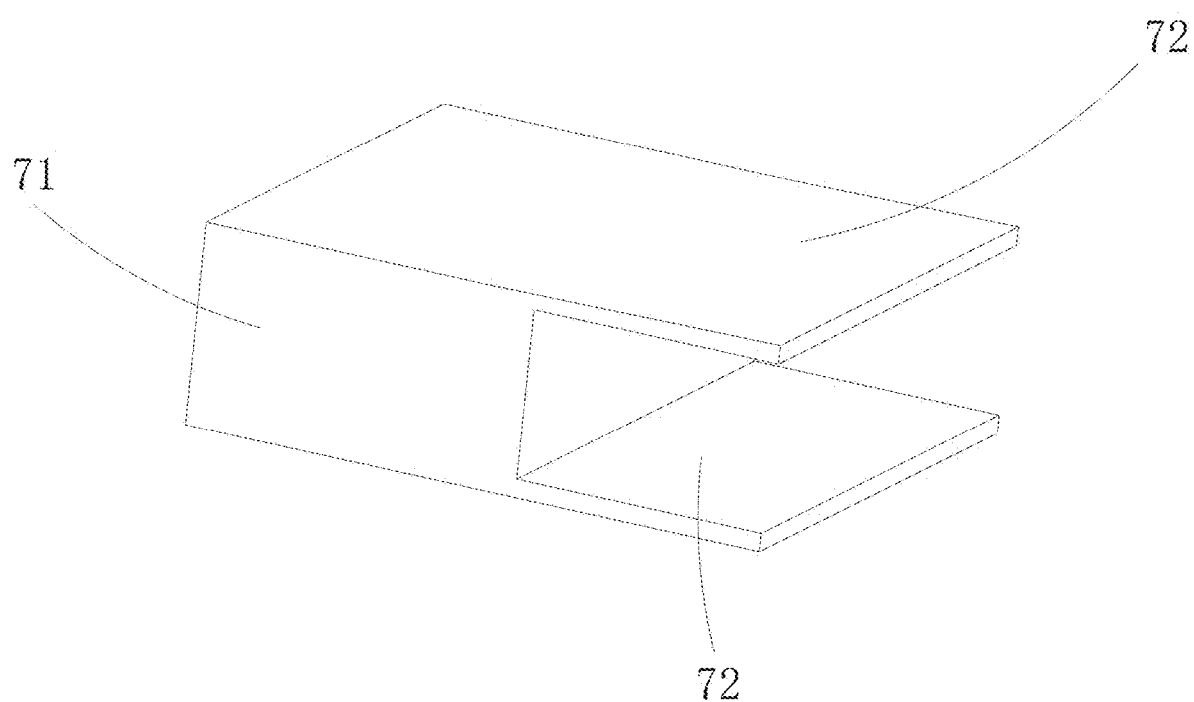
FIG. 18 is a structural schematic diagram of a shielding frame of a detector according to a ninth embodiment of the present disclosure.

In one alternative embodiment, please refer to FIGS. 16-18, a fixed hole 227 is provided on the detection circuit board 22; and the shielding assembly includes a shielding frame, the shielding frame includes a connecting plate 71a and two side baffles 72, the connecting plate 71 is worn in the fixed hole 227, and the two side baffles 72 are separately fixed to the two opposite ends of the connecting plate 71 to clamp the sensitive element 221.

When being sterilized, the detector can be placed below the irradiation source, the sensitive element 221 is located between the two side baffles 72, the connecting plate 71 is located at one end of the sensitive element 221, such structure can at least block the irradiation rays from three directions of the sensitive element 221, and the total-shadow shielding zone 801 formed by the two side baffles 72 and the connecting plate 71 covers the sensitive element 221, to protect the sensitive element 221 from being affected by the irradiation ray.

Figure 19:
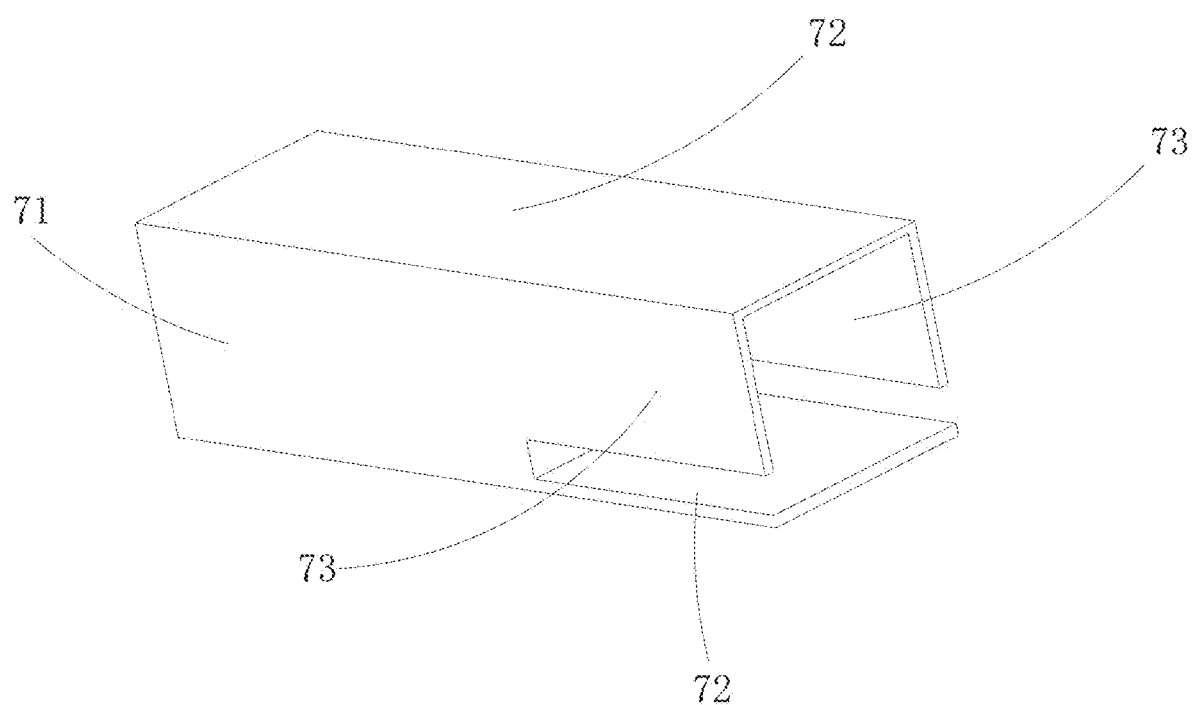
FIG. 19 is a structural schematic diagram of a shielding frame of a detector according to a tenth embodiment of the present disclosure.
Figure 20:
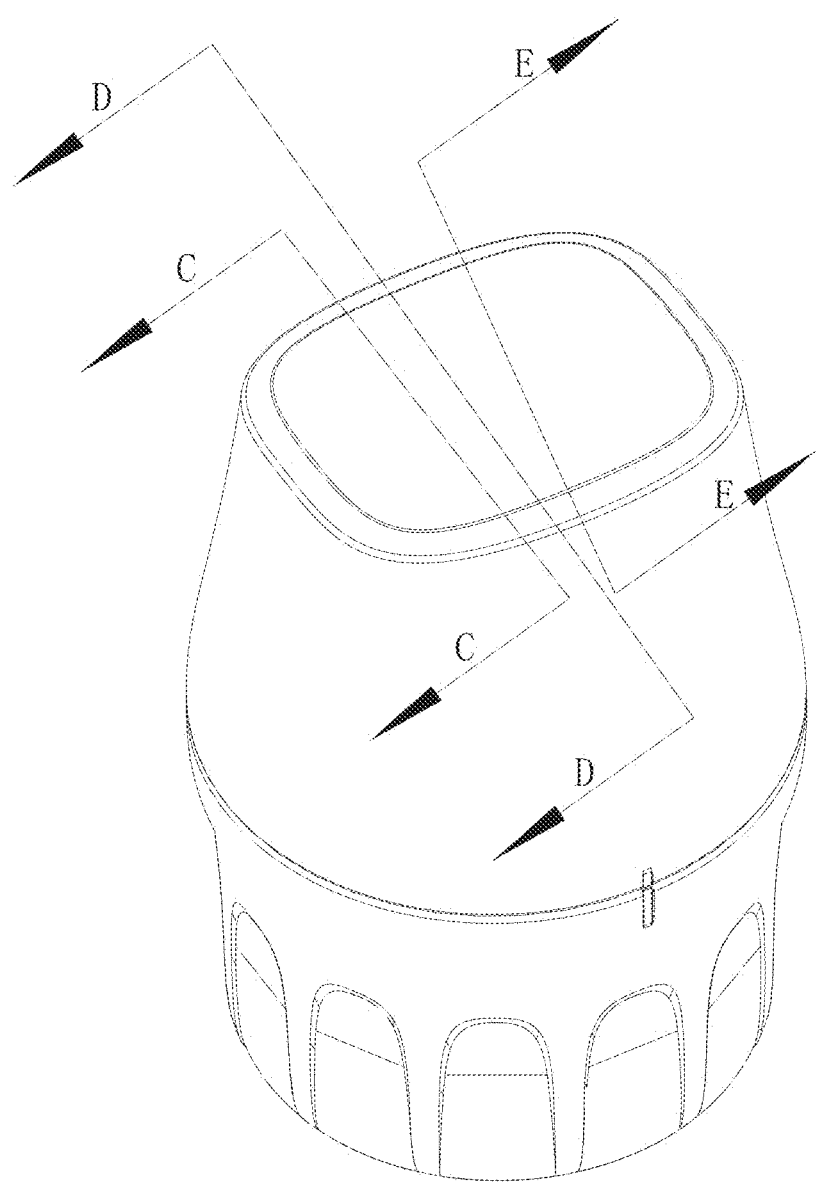
FIG. 20 is a solid diagram of a detector according to an eleventh embodiment of the present disclosure.

Further, as shown in FIG. 19, the shielding frame further includes vertical plates 73, the vertical plates 73 are located on one side of the detection circuit board 22 that is provided with the sensitive element 221, and one end of each of the vertical plates 73 is fixed to the two opposite ends of the side baffles 72 on this side.

The vertical plates 73 are disposed on the side baffles 72 and extend towards one side closing to the detection circuit board 22, such that the connecting plate 71, two side baffles 72 and two vertical plates 73 are separately located in five different directions of the sensitive element 221 and form the total-shadow shielding zone 801 for covering the sensitive element 221, thus better protecting the sensitive element 221 from being affected by the irradiation ray.

Alternatively, the shielding frame in the above embodiment specifically may be a component in the detection circuit board, such as a battery, an electromagnetic fastener and other components that can meet the function of shielding the irradiation ray.

Alternatively, the material of the shielding frame in the above embodiment is the same as that of the shielding block 80, both of which can achieve the function of blocking the irradiation ray.

It can be understood that the shape of the shielding frame is not limited to the above solution, and can be set according to specific demands, for example, the section of the shielding frame may also be a curved surface, a polygon and the like as long as the total-shadow shielding zone formed by the shielding frame can wrap the sensitive element.

Please combine with FIGS. 20-27, embodiments of the present disclosure further provide a detector, the detector has the structure that is basically the same as that of the detector in the above embodiments, where the components with the structures that are basically the same adopt the same number, the above components are not repeatedly described any more, and the key part of the detector provided by this embodiment and the part different from other embodiments are mainly described below.

Figure 21:
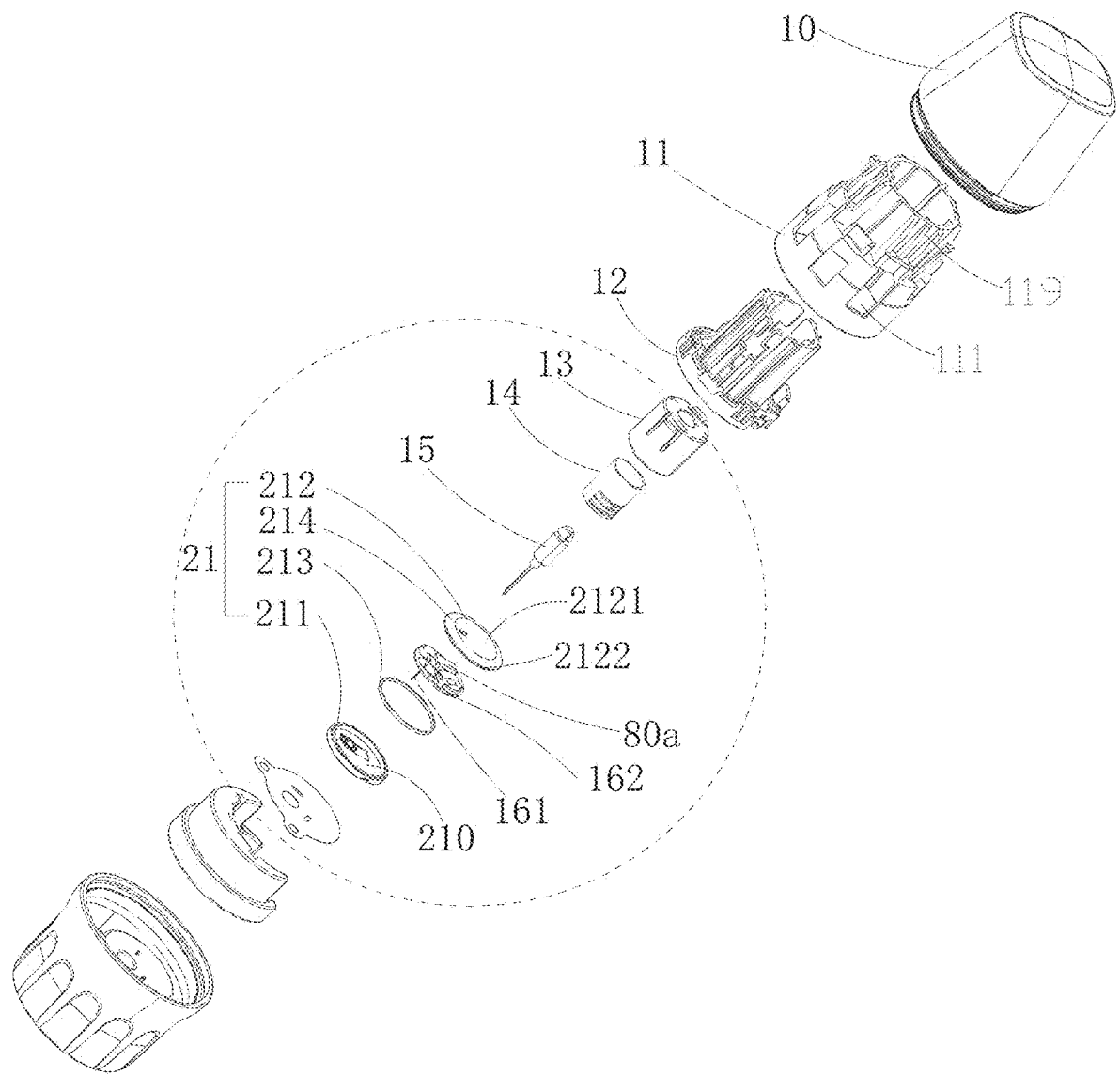
FIG. 21 is an exploded view of a detector according to an eleventh embodiment of the present disclosure.
Figure 22:
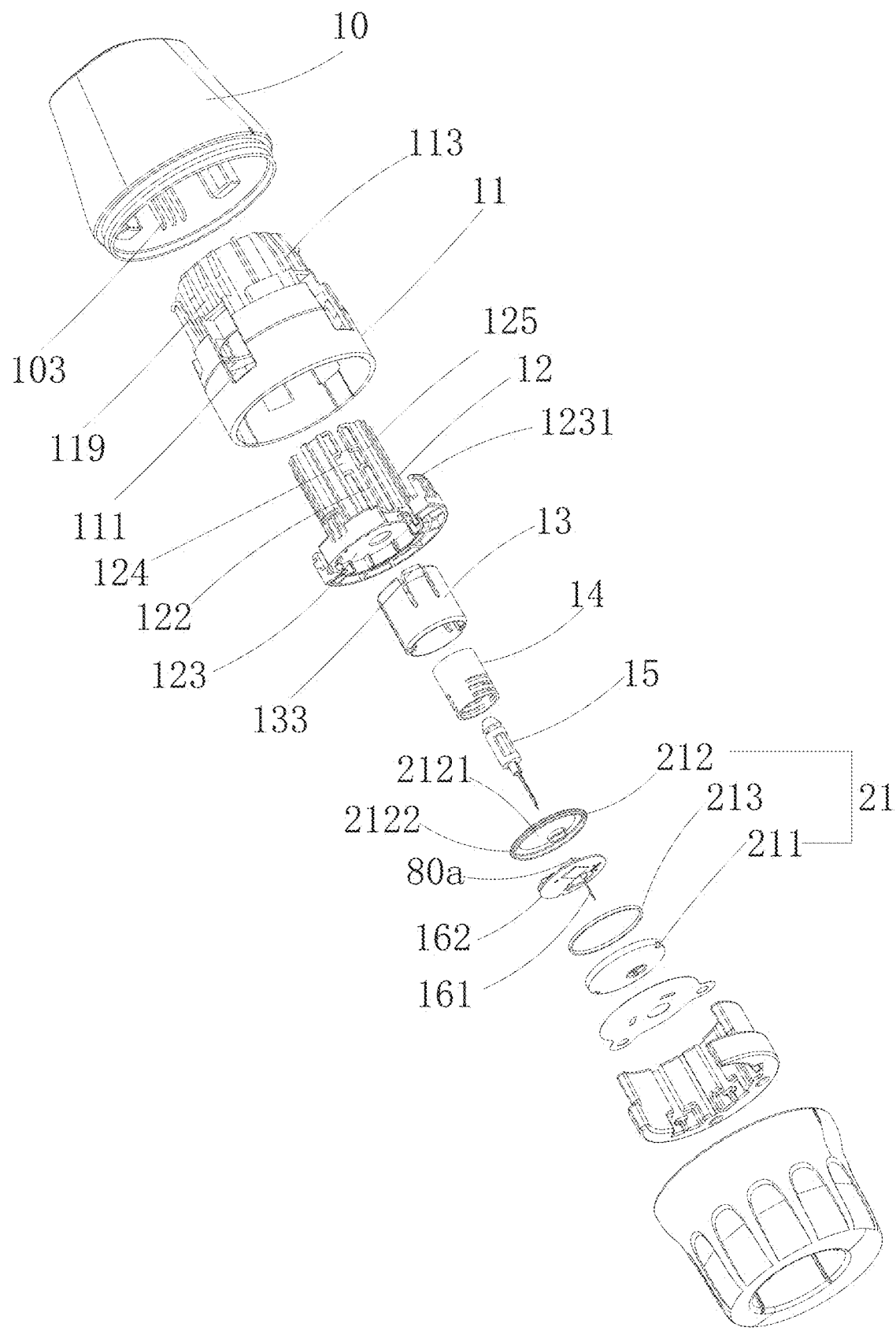
FIG. 22 is an exploded view in another angle of a detector according to an eleventh embodiment of the present disclosure.

Specifically, please refer to FIG. 21 and FIG. 22, in this embodiment, the first housing 21 includes a bearing shell 211, a cover body 212 and a sealing element 213, the bearing shell 211 is hermetically connected with the cover body 212 through the sealing element 213 and forms a sealed storage cavity 210, the detection circuit board 22 is located in the storage cavity 210, and it can be understood that the sealing area of the total-shadow shielding zone includes the storage cavity 210. Hermetically arranging the detection circuit board 22 in the first housing 21 as a whole can more effectively reduce the pollution situation possibly generated when the detection circuit board 22 is not sterilized, to ensure the safety and accuracy of the detection.

Further, the first housing 21 has a cut-through hole 214, one end of the probe 161 is located in the cut-through hole 214 and stretches into the first housing 21 by passing through a connector 163 of a hole wall of the cut-through hole 214 to be electrically connected with the detection circuit board 162, the other end of the probe 161 stretches out of the cut-through hole 214 and extends towards a direction away from the pressing portion, the guide needle 15 includes a connecting rod 151 and a needle body 152 connected with the connecting rod 151, the connecting rod 151 is connected with the support bracket 13, and the needle body 152 is provided with a through hole that accommodates the probe 161 and is slidingly connected with the probe 161.

It can be understood that, in other embodiments, at least one of the bearing shell 211 and the cover body 212 may be made of a flexible material, such as silica gel, and at this time, the sealing element 213 may be omitted, that is, the bearing shell 211 and the cover body 212 can be directly and hermetically connected.

Further, the bearing shell 211 may include a bearing plate 2111 and a side wall structure 2112 connected with the bearing plate 2111, the side wall structure 2112 is provided with a sealing slot 2113, at least part of the sealing element 213 is located in the sealing slot 2113, the cover body 212 includes a main cover body 2121 and a raised structure 2122 that is connected with the main cover body 2121 and extends towards one side of the bearing plate 2111, the raised structure 2122 is used for resisting and connecting the sealing element 213, and the sealing element 213 may include a sealant, a sealing rubber ring or a combination of the sealant and the sealing rubber ring.

Figure 23:
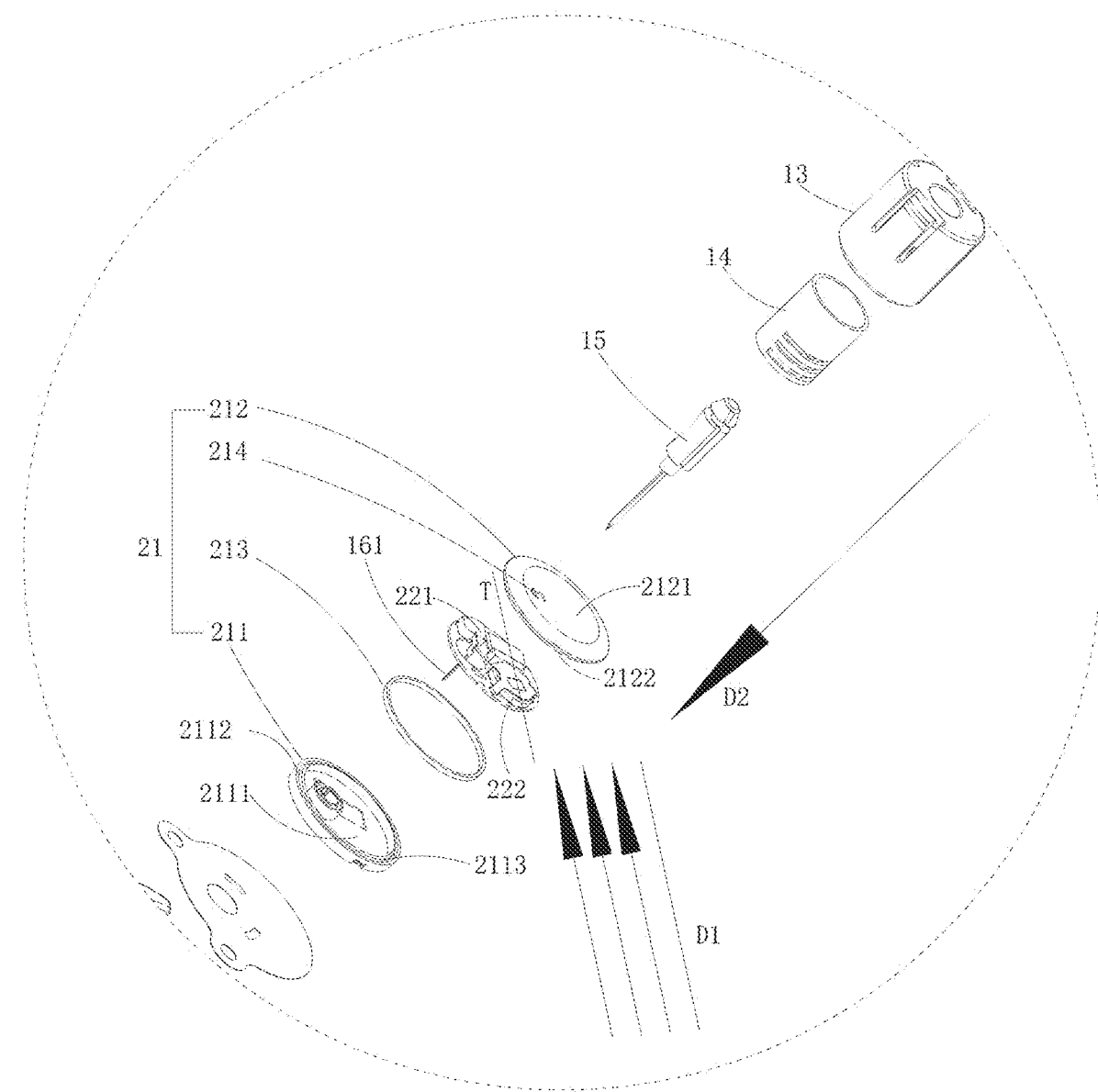
FIG. 23 is a partial structural schematic diagram of a detector according to an eleventh embodiment of the present disclosure.
Figure 24:
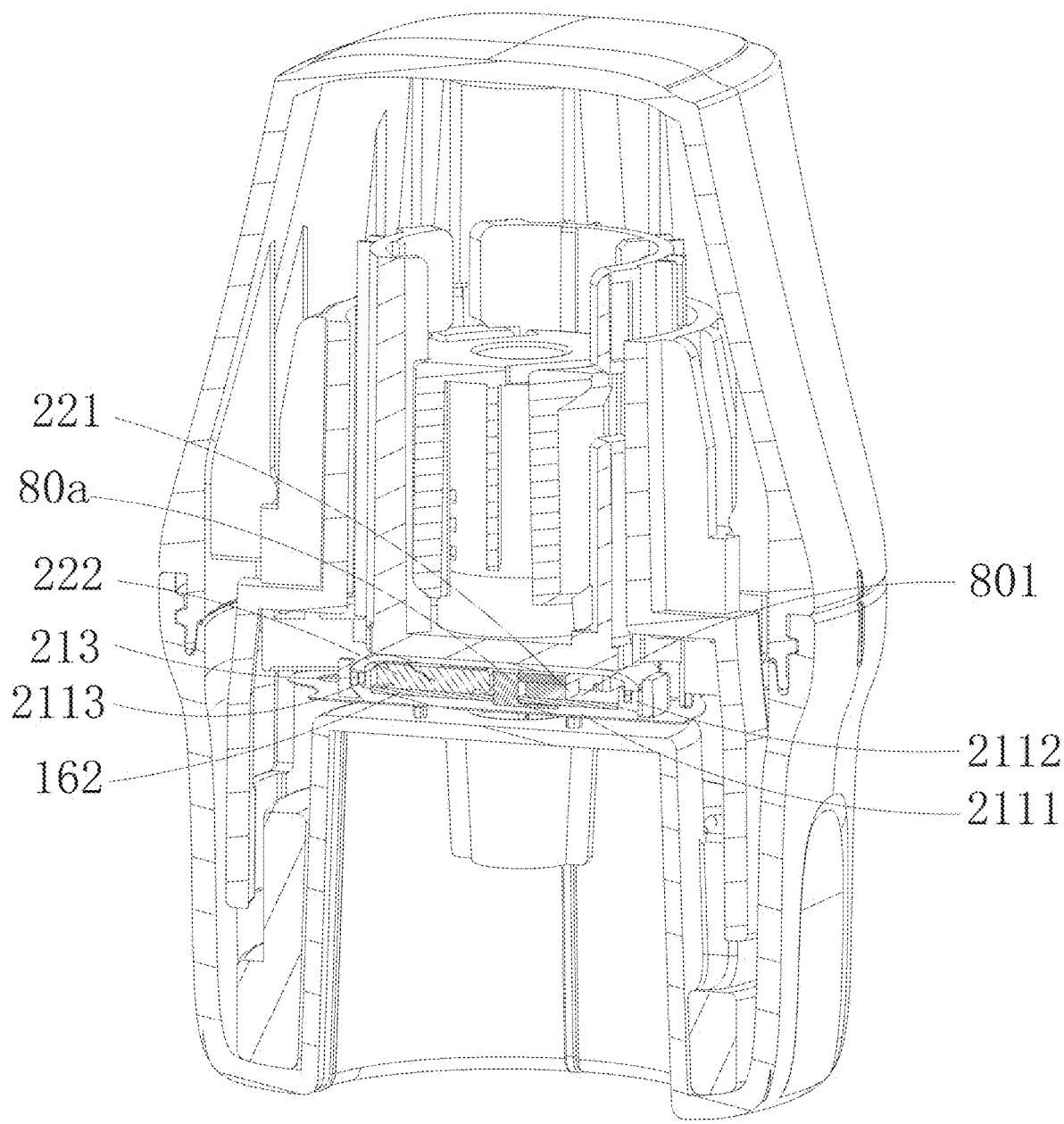
FIG. 24 is a profile diagram along a line C-C in FIG. 20.

More further, please refer to FIG. 23, the shielding assembly 80a is disposed on the detection circuit board 22, the shielding assembly 80a and the sensitive element 221 are arranged on a path T that an irradiation source for sterilization is emitted to the detector, such that the shielding assembly 80a can block a radiation of the irradiation source to be emitted to the sensitive element 221, and an irradiation direction D1 of the radiation is different from a pressing direction D2 of the pressing portion, and specifically, the irradiation direction D1 of the radiation may be perpendicular to the pressing direction D2 of the pressing portion.

The detection circuit board 22 is also provided with a battery module 222, the battery module 222, the shielding assembly 82a and the sensitive element 221 are all disposed on the path T that the irradiation source for sterilization is emitted to the detector, such that the battery module 222 and shielding assembly 80a block the radiation of the irradiation source to be emitted to the sensitive element together. It can be understood that, in other embodiments, the battery module 222 may also be replaced with other electronic devices, such as inductance, capacitance, resistance, chips or other devices.

Further, as shown in FIGS. 20-27, the detector includes a housing 10, a first barrel-shaped bracket 11, a second barrel-shaped bracket 12, a support bracket 13, an elastic element 14, a guide needle 15 and a detection assembly;

the first barrel-shaped bracket 11 is slidingly located in the housing 10 and partially located in the housing 10;

the second barrel-shaped bracket 12 is slidingly located in the first barrel-shaped bracket 11 and connected with the housing 10 through an extending connecting portion 1231, and a first through hole 124 is provided on the second barrel-shaped bracket 12;

the support bracket 13 is located in the second barrel-shaped bracket 12, and an elastic resisting portion 133 extends outside the support bracket 13;

the elastic element 14 is compressed between the second barrel-shaped bracket and the support bracket 13, such that the elastic resisting portion 133 abuts against the hole wall of the first through hole 124;

the guide needle 15 is connected with the support bracket 13, an accommodating slot 154 is provided on the guide needle 15, and the guide needle 15 is used for piercing into the sampling part;

the detection assembly is connected with one side of the first base plate 123 that is away from a second base plate of the support bracket 13, and the detection assembly includes a probe 161 that is partially accommodated in the accommodating slot 154; and the housing 10 is used for driving the second barrel-shaped bracket to move in relative to the first barrel-shaped bracket 11, when the second barrel-shaped bracket moves to the first preset position, the guide needle 15 is pierced into the sampling part, and when moving to the second preset position, the elastic resisting portion 133 shrinks inward, such that the elastic element 14 drives the guide needle 15 to leave the sampling part.

The detection assembly can be used for detecting various data of the human body, including but not being limited to blood glucose indexes, hemoglobin, white blood cell count, blood platelet count and the like, and the following embodiments take the detection for blood glucose indexes as an example.

In the embodiments of the present disclosure, the elastic element 14 may be a spring. Since the elastic element 14 is compressed between the second barrel-shaped bracket the support bracket 13, that is, the elastic element 14 will apply an elastic force to the second barrel-shaped bracket and the support bracket 13 to enable the second barrel-shaped bracket to be away from the support bracket 13, but the elastic resisting portion 133 abuts against the hole wall of the first through hole 124, such that the elastic force generated by the elastic element 14 is applied on the hole wall of the first through hole 124 through the elastic resisting portion 133, the second barrel-shaped bracket and the support bracket 13 are also stationary relatively, and the elastic element 14 keeps a state of being compressed.

When the user adopts the detector for detecting the blood glucose, the user holds the housing 10 and aligns the detection assembly with the sampling part, the first barrel-shaped bracket 11 abuts against a vicinity of the sampling portion, and at this time the guide needle 15 is not in contact with the sampling part. Then the housing 10 is pushed to move towards one side closing to the sampling part; since the housing 10 is connected with the second barrel-shaped bracket, the support bracket 13 also abuts against the second barrel-shaped bracket through the elastic resisting portion 133, the housing 10 can drive the support bracket 13, guide needle 15 and detection assembly to move towards one side closing to the sampling part when driving the second barrel-shaped bracket to move. In a process that the second barrel-shaped bracket drives the guide needle 15 to move, the guide needle 15 is close to the sampling part gradually until the second barrel-shaped bracket moves to the first preset position, and the guide needle 15 is pierced into the sampling part. Specifically, due to insufficient hardness of the probe 161, the probe 161 is accommodated in the accommodating slot 154, and the probe 161 is brought into the sampling part by piercing the detection assembly into the sampling part, thus sampling through the probe 161 and detecting the blood glucose indexes.

The user continues to push the housing 10 to move towards one side closing to the sampling part until the second barrel-shaped bracket reaches the second preset position. At this time, the elastic resisting portion 133 moves towards one side of a first guide wall 126 that is away from the housing 10, that is, the elastic resisting portion 133 shrinks inward, such that the elastic resisting portion 133 moves out of the first through hole 124. The elastic resisting portion 133 does not abut against the hole wall of the first through hole 124 any more, the support bracket 13 is also not limited by the second barrel-shaped bracket any more, the elastic force generated by the compressed spring will push the support bracket 13 towards one side away from the first base plate 123, thus driving the guide needle 15 to move towards one side away from the sampling part, enabling the guide needle 15 to leave a to-be-sampled part, and quickly pulling out the guide needle 15 from the sampling part. Since the detection assembly is not connected with the support bracket 13, the probe 161 of the detection assembly will not be pulled out of the sampling part together with the guide needle 15, instead of remaining in the sampling part for continuous sampling detection, thus dynamically feeding back a detection result.

Through the above embodiments, the user may push the housing 10, the probe 161 is pierced into the sampling part through the guide needle 15, the support bracket 13 is not limited by the second barrel-shaped bracket any more after the guide needle 15 brings the probe 161 into the sampling part for a certain depth, the spring is released such that the guide needle 15 is quickly pulled out of the sampling part along the piercing path, so situations of strong pain, skin injury and the like of to-be-detected personnel, caused by deviating from the trajectory, relatively slow needle withdrawal and the like, do not appear easily, thus improving the experience of the to-be-detected personnel.

In one alternative embodiment, the specific structure of the detector is that the first barrel-shaped bracket 11 is partially located in the housing 10. The first barrel-shaped bracket 11 forms a cylinder of which two ends are cut-through, and the cylinder has a first cavity; and a travel hole 111 is provided on an outer wall of the first barrel-shaped bracket 11, and the travel hole 111 may be specifically a strip hole; and the second barrel-shaped bracket includes a first base plate 123 and a first guide wall 126, the first base plate 123 is provided with a connecting portion 1231, the connecting portion 1231 passes through the travel hole 111 and is connected with the housing 10, and the connecting portion 1231 can move along a length direction of the travel hole 111; and the travel hole 111 may limit the moving direction and maximum distance of the connecting portion 1231. The first guide wall 126 is perpendicular to one side of the first base plate 123 and encloses a second cavity, and the first through hole 124 is provided on the first guide wall 126; and the support bracket 13 is located in the second cavity.

On the one hand, the first guide wall 126 can limit the position of the support bracket 13, allowing the support bracket 13 not to generate a horizontal displacement easily in relative to the second barrel-shaped bracket; and on the other hand, the piercing direction of the guide needle 15 is enabled to be consistent with the pull-out direction thereof, to avoid injuries on the to-be-detected user due to inconsistent piercing and pull-out directions.

In one alternative embodiment, a support wall is provided on the first barrel-shaped bracket 11, and the support wall extends towards one side of the sampling part and is used for abutting against the sampling part.

The support wall is used for abutting against the sampling part, and a length of the support wall is greater than a distance from the guide needle 15 to the sampling part, such that the travel space of the guide needle 15 is reserved by the support wall abutting against the sampling part.

In one alternative embodiment, a first guide portion 113 is provided on the first barrel-shaped bracket 11, the first guide portion 113 is partially located in the first through hole 124, and when the detection assembly moves to the second preset position, the first guide portion 113 extrudes the elastic resisting portion 133 from the first through hole 124.

In a process that the second barrel-shaped bracket is driven to move closely to the sampling part along the length direction of the travel hole 111 when the user pushes the housing 10, the elastic resisting portion 133 approaches to the first guide portion 113 gradually. The elastic resisting portion 133 and the first guide portion 113 are relatively provided with two inclined surfaces, and in a process when the detection assembly moves to the second preset position, the inclined surface of the elastic resisting portion 133 is in contact with that of a first resisting portion, the elastic resisting portion 133 shrinks inward along the inclined surface of the first guide portion 113, such that the first guide portion 113 extrudes the elastic resisting portion 133 from the first through hole 124 along the inclined surface of the first guide portion 113. The second barrel-shaped bracket does not limit the elastic resisting portion 133 any more, and the elastic element 14 is released such that the support bracket 13 moves towards one side away from the sampling part, thus pulling the guide needle 15 out of the sampling part.

In one alternative embodiment, a second through hole (not shown in the drawing) is provided on the first base plate 123, and the guide needle 15 includes:

a connecting rod 151, where the connecting rod 151 penetrates through the second through hole and includes a first end and a second end that are opposite to each other, and the first end is fixed to the support bracket 13;

a needle body 152, where the needle body 152 is connected with the second end of the connecting rod 151, an accommodating slot 154 is provided on the needle body 152, and please refer to FIG. 23 for details.

The support bracket 13 drives the connecting rod 151 to move, thus driving the needle body 152 to move, thereby enabling the needle body 152 to be pierced into or pulled out of the sampling part. Since the probe 161 is accommodated in the accommodating slot 154, the probe 161 also enters the sampling part together when the needle body 152 is pierced into the sampling part.

Further, the detection assembly includes:

a detection circuit board 162, where the detection circuit board 162 is connected with one side of the first base plate 123 that is away from the support bracket 13, and used for connecting with the probe 161.

The detection circuit board 162 is also used for receiving the information detected after the probe 161 enters the sampling part. The detection circuit board 162 may also transmit the information received to other terminals, so as to inform the users of the specific information detected in various forms (such as characters and charts).

In one alternative embodiment, an inner wall of the housing 10 is provided with an arc-shaped bulge 101, and the arc-shaped bulge 101 is located on one side of the first base plate 123 that faces the first guide wall 126; and an outer wall of the first barrel-shaped bracket 11 is provided with a first limiting portion 117, and the first limiting portion 117 is located between the arc-shaped bulge 101 and the first base plate 123 and abuts against the arc-shaped bulge 101.

The user operates the housing 10 to move towards one side closing to the sampling part, and before the second barrel-shaped bracket moves to the second preset position, the first limiting portion 117 will abut against the arc-shaped bulge 101. After contacting with the arc-shaped bulge 101, the user applies a relatively great thrust to the housing 10 since the first limiting portion 117 has a certain elasticity, such that the first limiting portion 117 exceeds the arc-shaped bulge 101 gradually.

However, the speed that the user pushes the housing 10 becomes slow due to the interference on the first limiting portion 117 by the arc-shaped bulge 101, after the first limiting portion 117 moves to the highest point of the arc-shaped bulge 101, the first barrel-shaped bracket 11 is not interfered by the first limiting portion 117 any more, the user will keep a relatively great thrust due to inertia, such that the housing 10 and the whole second barrel-shaped bracket have a relatively great accelerated speed to move towards one side of the sampling part at a moment that the first limiting portion 117 exceeds the highest point of the arc-shaped bulge 101, thus quickly piercing a needling component into the sampling part. When the user has not yet felt the pain of piercing into the sampling part completely, the guide needle 15 has been pierced into the sampling part, to avoid generating a great pain when slowing down the piercing process due to the user's pain.

In one alternative embodiment, a first guide slot 125 is provided on the outer wall of the second barrel-shaped bracket, and a second guide portion (not shown in the drawings) corresponding to the first guide slot 125 is provided on the inner wall of the first barrel-shaped bracket 11; and the first guide slot 125 is used for limiting the moving direction of the second guide portion.

When the user controls the movement of the housing 10, the housing 10 drives the second barrel-shaped bracket to move, the second guide portion moves along the direction of the first guide slot 125, thus limiting the movement of the housing 10 and the second barrel-shaped bracket, and avoiding the deviation generated by unstable movement due to improper user operations.

In one alternative embodiment, a second guide slot 119 is provided on the outer wall of the first barrel-shaped bracket 11, and a third guide portion 103 corresponding to the second guide slot 119 is provided on the inner wall of the housing 10; and the second guide slot 119 is used for limiting the moving direction of the third guide portion 103.

The cooperative effect of the second guide slot 119 and the third guide portion 103 is basically the same as that of the first guide slot 125 and the second guide portion, both of which are used for avoiding the deviation generated by unstable movement due to improper user operations, and repetitions are not made here.

Figure 25:
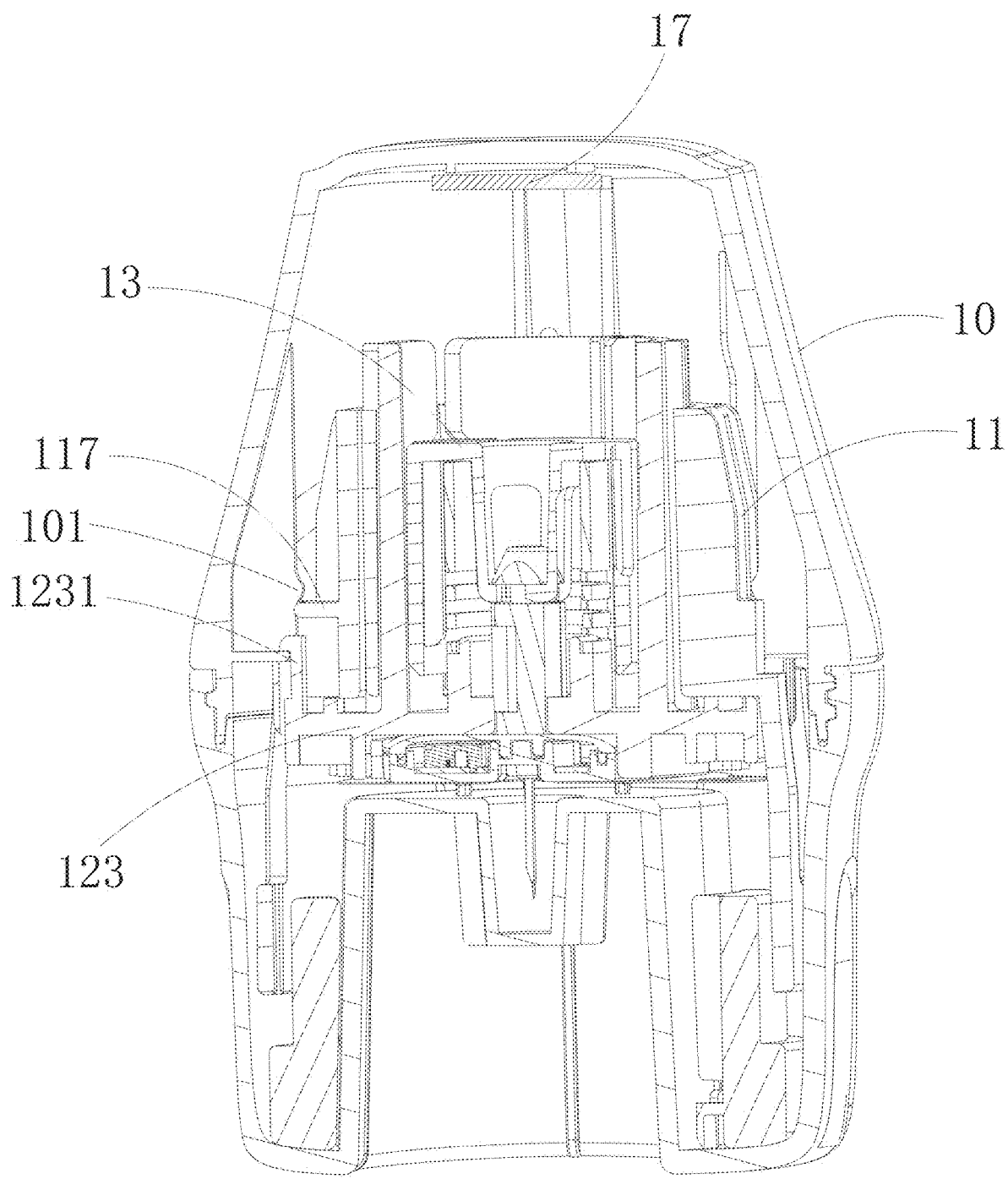
FIG. 25 is a profile diagram along a line D-D in FIG. 20.
Figure 26:
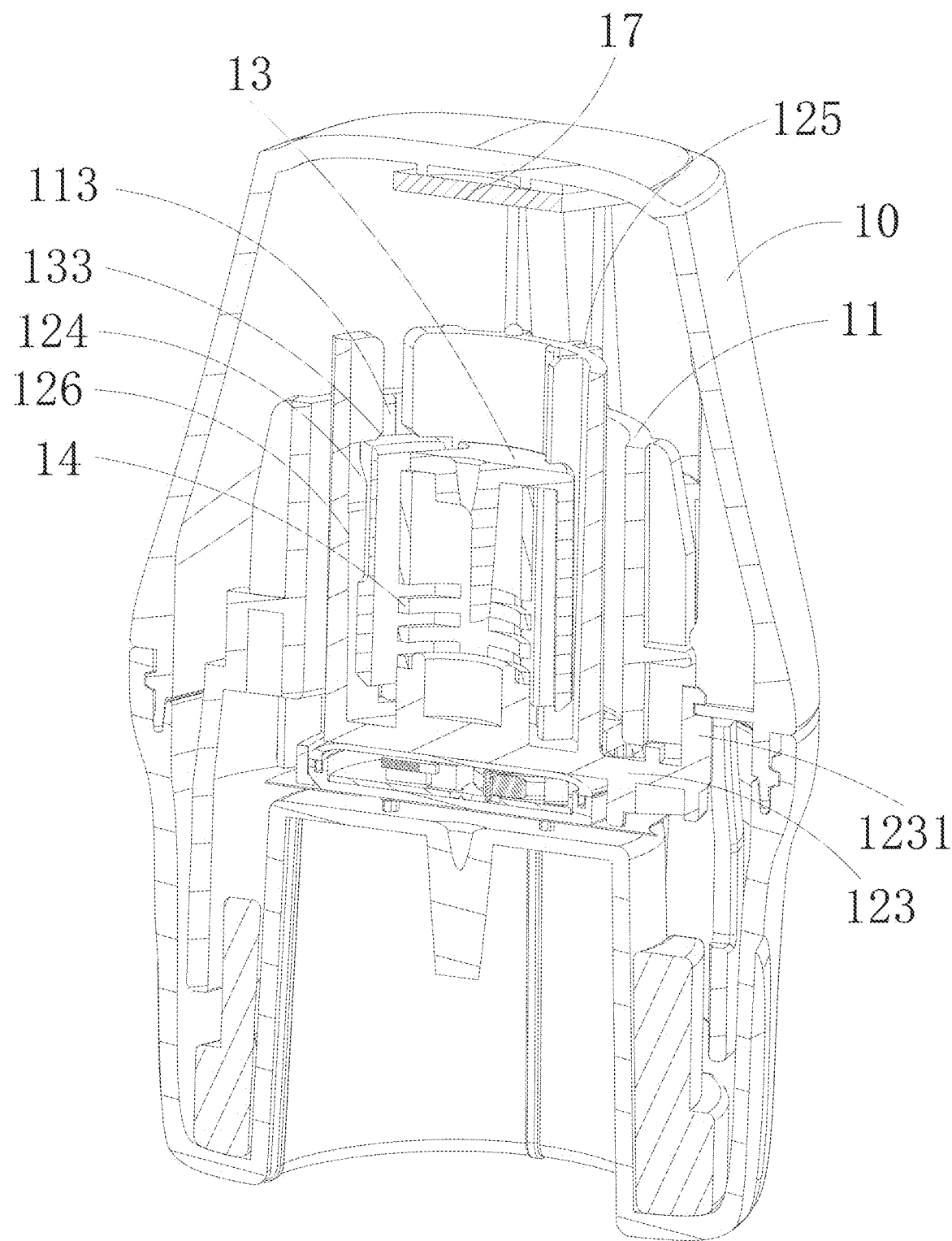
FIG. 26 is a profile diagram along a line E-E in FIG. 20.
Figure 27:
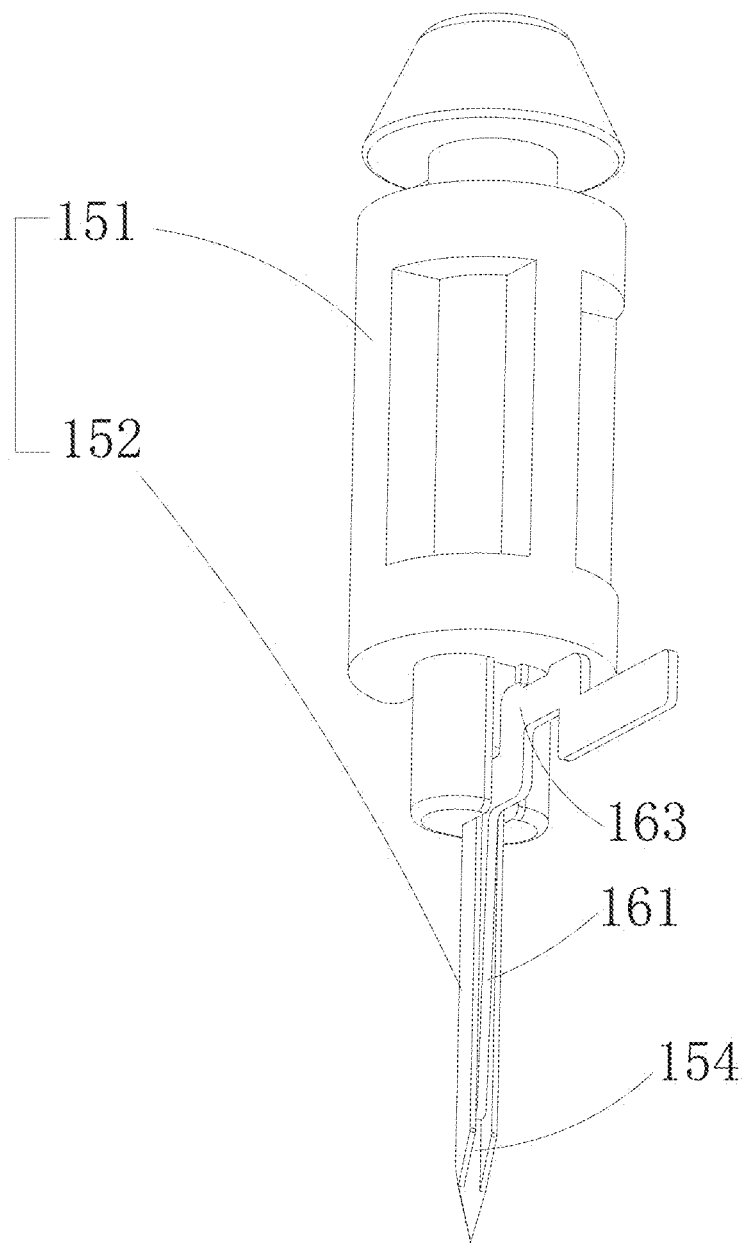
FIG. 27 is a partial structural schematic diagram of a detector according to an eleventh embodiment of the present disclosure.

In one alternative embodiment, please refer to FIG. 25 and FIG. 26, the detector further includes a shock absorbing assembly 17, and the shock absorbing assembly 17 is located on one side of the support bracket 13 that is away from the first base plate 123 and fixed to the inner wall of the housing 10.

The elastic force, generated when the elastic element 14 is released, will push the support bracket 13 towards one side, and the support bracket 13 will collide with the housing 10 to generate a vibration, which may cause the guide needle 15 to generate the deviation. However, the shock absorbing assembly 17 can replace the housing 10 to bear the shock generated by the support bracket 13, and weaken the vibration brought by the shock, thus avoiding the deviation of the guide needle 15 caused by the vibration. Specifically, the shock absorbing assembly 17 may be a sponge mat.

Figure 28:
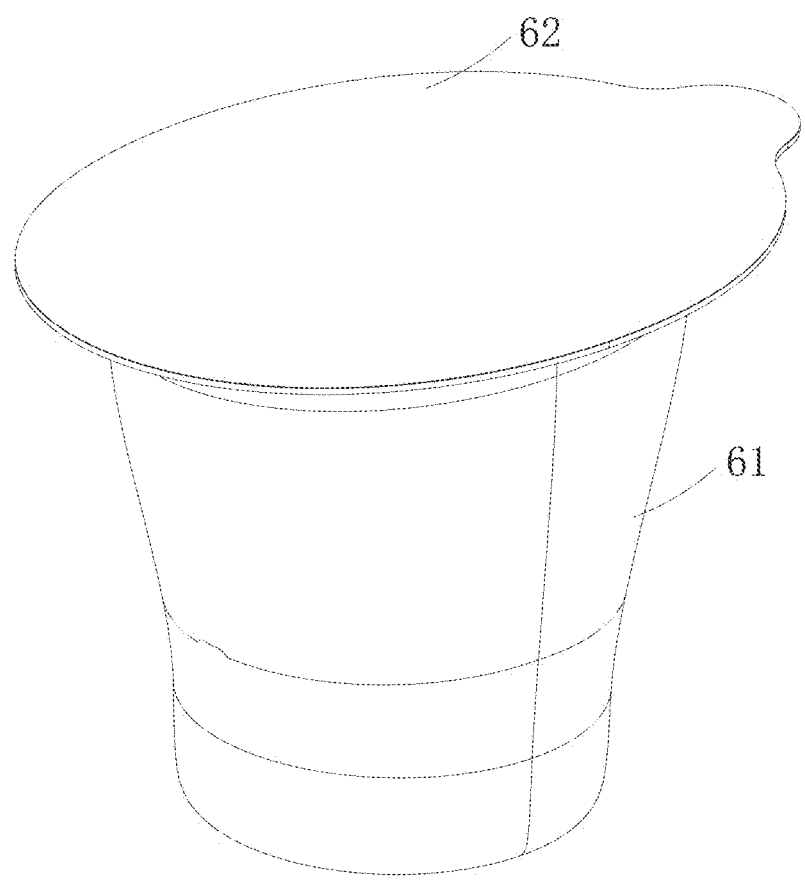
FIG. 28 is a schematic diagram of an outer package of a detector according to embodiments of the present disclosure.
Figure 29:
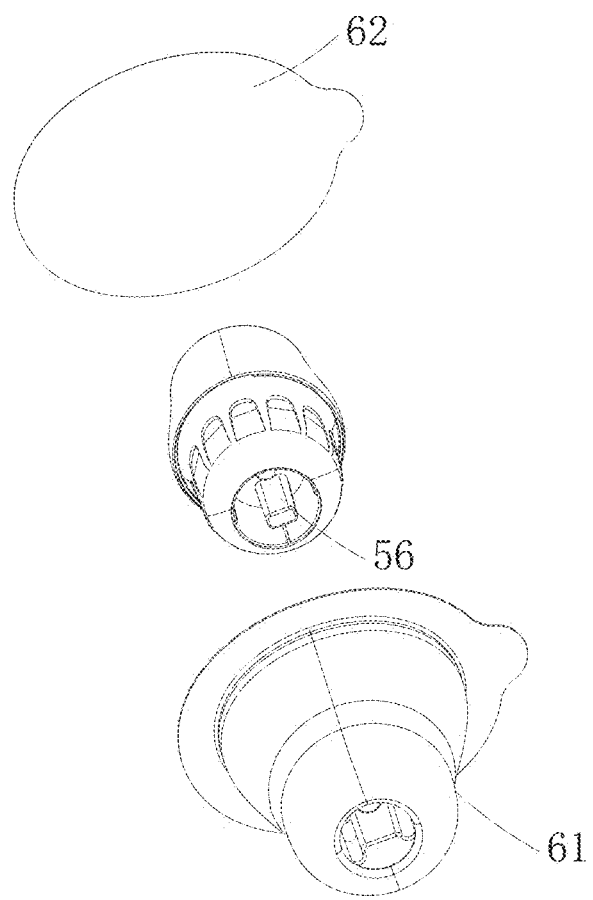
FIG. 29 is an exploded view of an outer package shown in FIG. 28.
Figure 30:
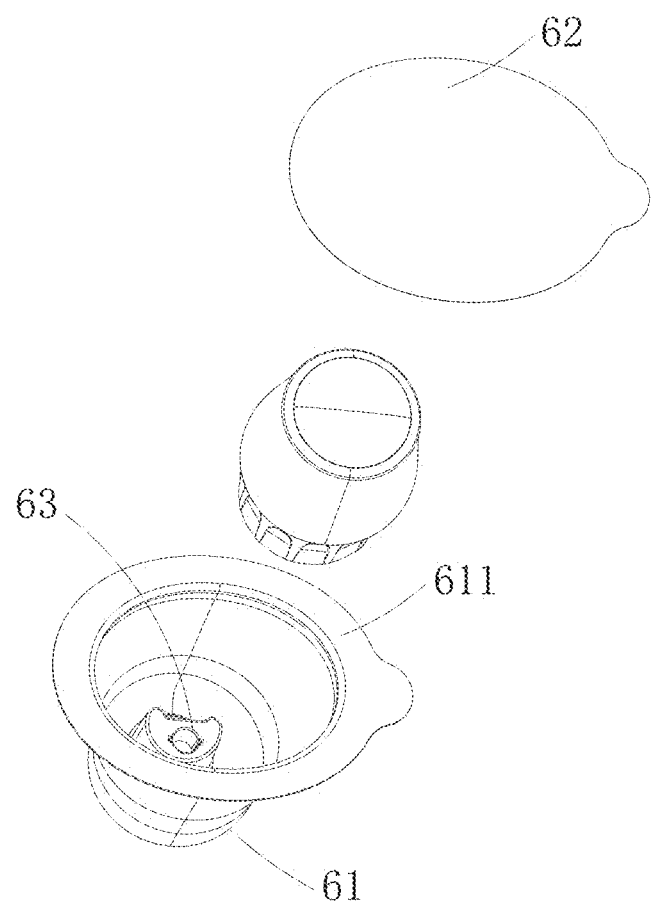
FIG. 30 is an exploded view in another angle of an outer package shown in FIG. 28.

Please refer to FIGS. 28-30, embodiments of the present disclosure further provide a detector assembly, the detector assembly may adopt the detector in any one of the above embodiments and the outer package for sealing and packaging the detector, the outer package may include a main housing 61 and an easy-to-tear film 62, the main housing 61 is provided with an accommodating space and an opening communicating with the accommodating space, the main housing 61 has an end face 611 surrounding the opening, an outer contour of the easy-to-tear film 62 is basically consistent with that of the end face 611, and the easy-to-tear film 62 is attached to the end face 611 through colloid; and the main housing 61 is also provided with a first counterpoint structure 63, the bottom of the detector (such as on the second outer shell 52) may have a second counterpoint structure 56, and the second counterpoint structure 56 is in counterpoint fit with the first counterpoint structure 63, such that the detector may be disposed in the main housing 61 according to a preset orientation.

Figure 31:
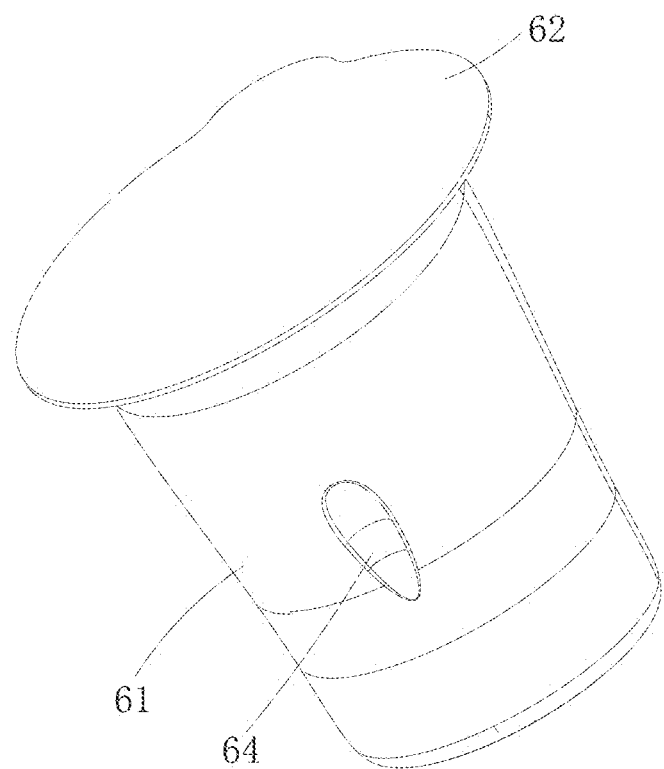
FIG. 31 is a schematic diagram of an outer package of a detector according to another embodiment of the present disclosure.
Figure 32:
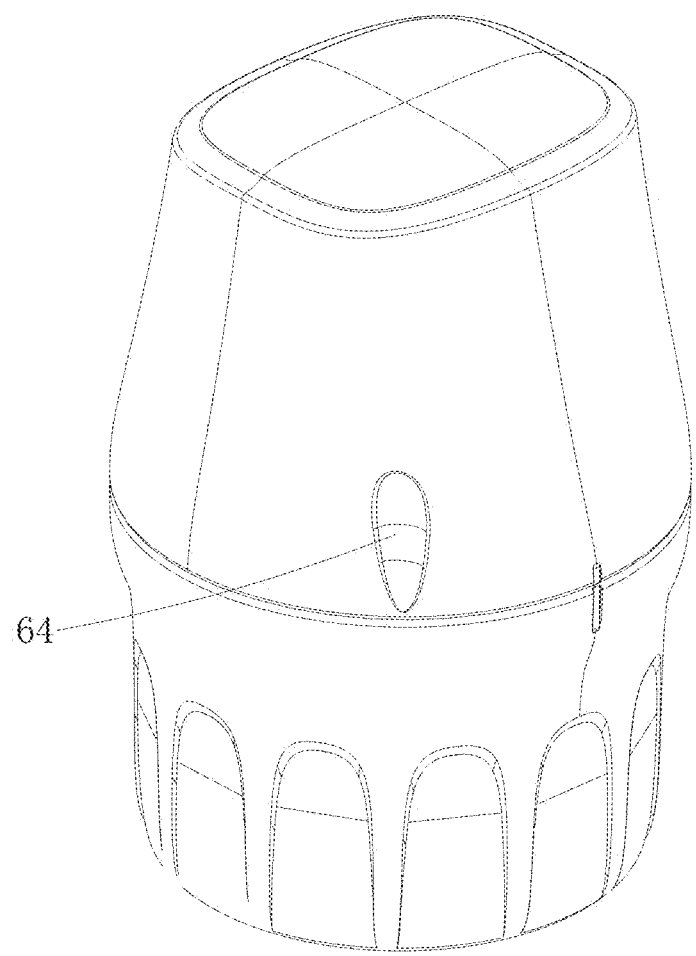
FIG. 32 is a schematic diagram of a detector according to another embodiment of the present disclosure.
Figure 33:
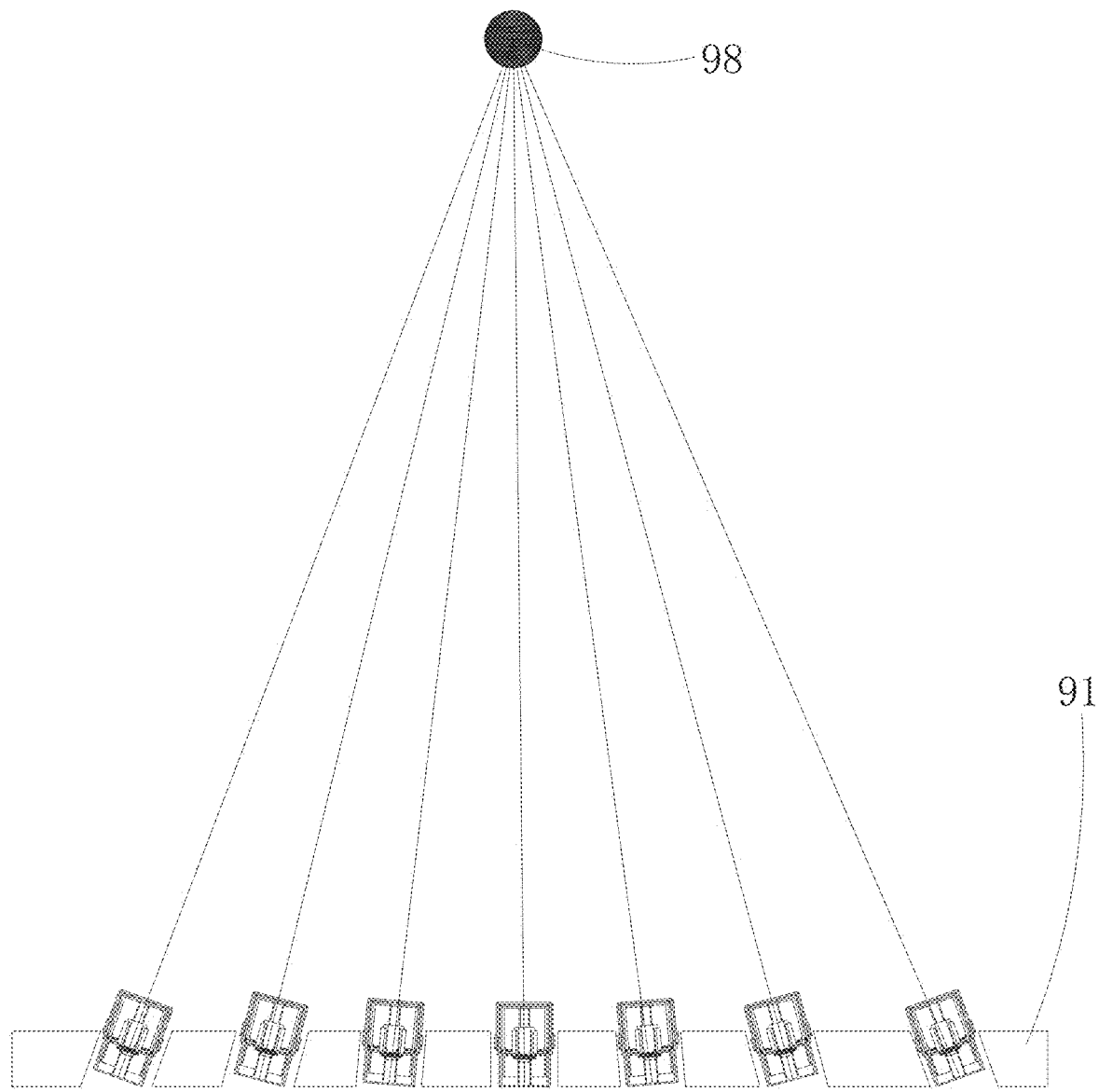
FIG. 33 is a structural schematic diagram of a sterilization system according to embodiments of the present disclosure.
Figure 34:
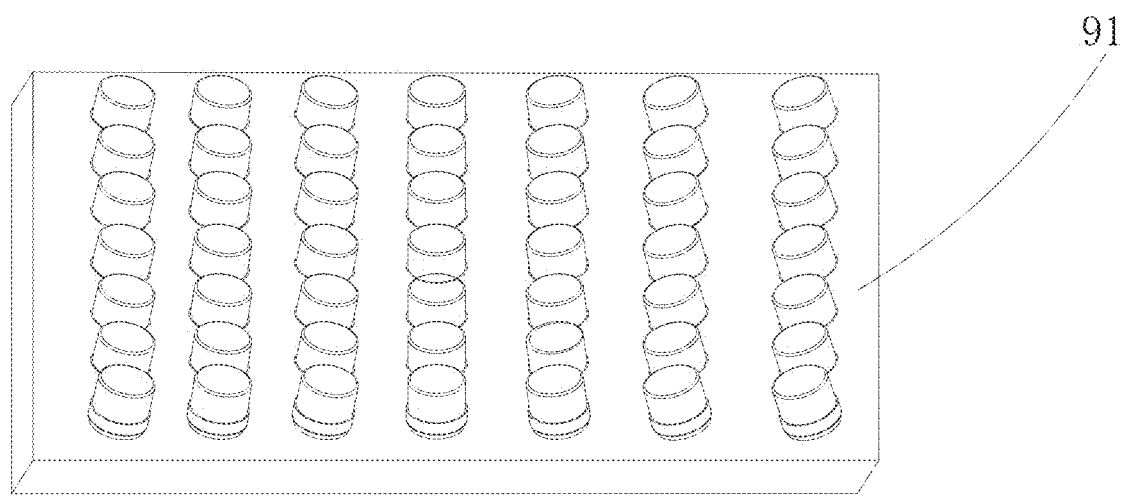
FIG. 34 is a structural schematic diagram of a bearing frame of a sterilization system according to embodiments of the present disclosure.
Figure 35:
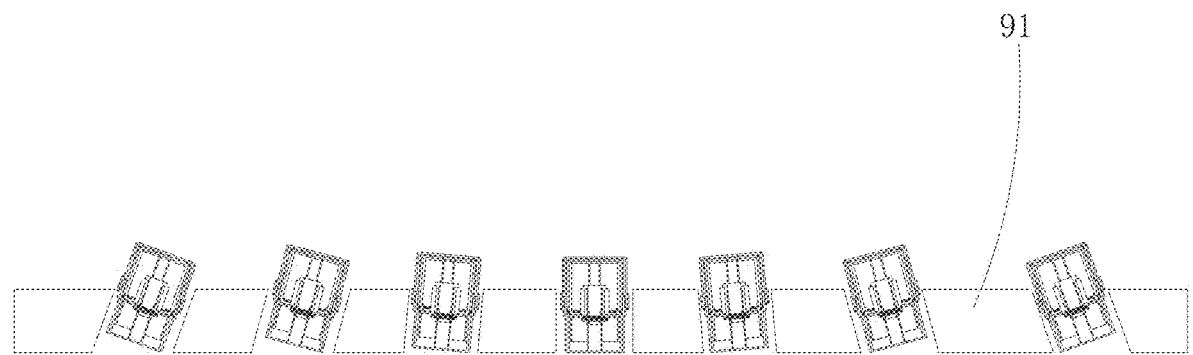
FIG. 35 is a profile diagram of a bearing frame of a sterilization system according to embodiments of the present disclosure.
Figure 36:
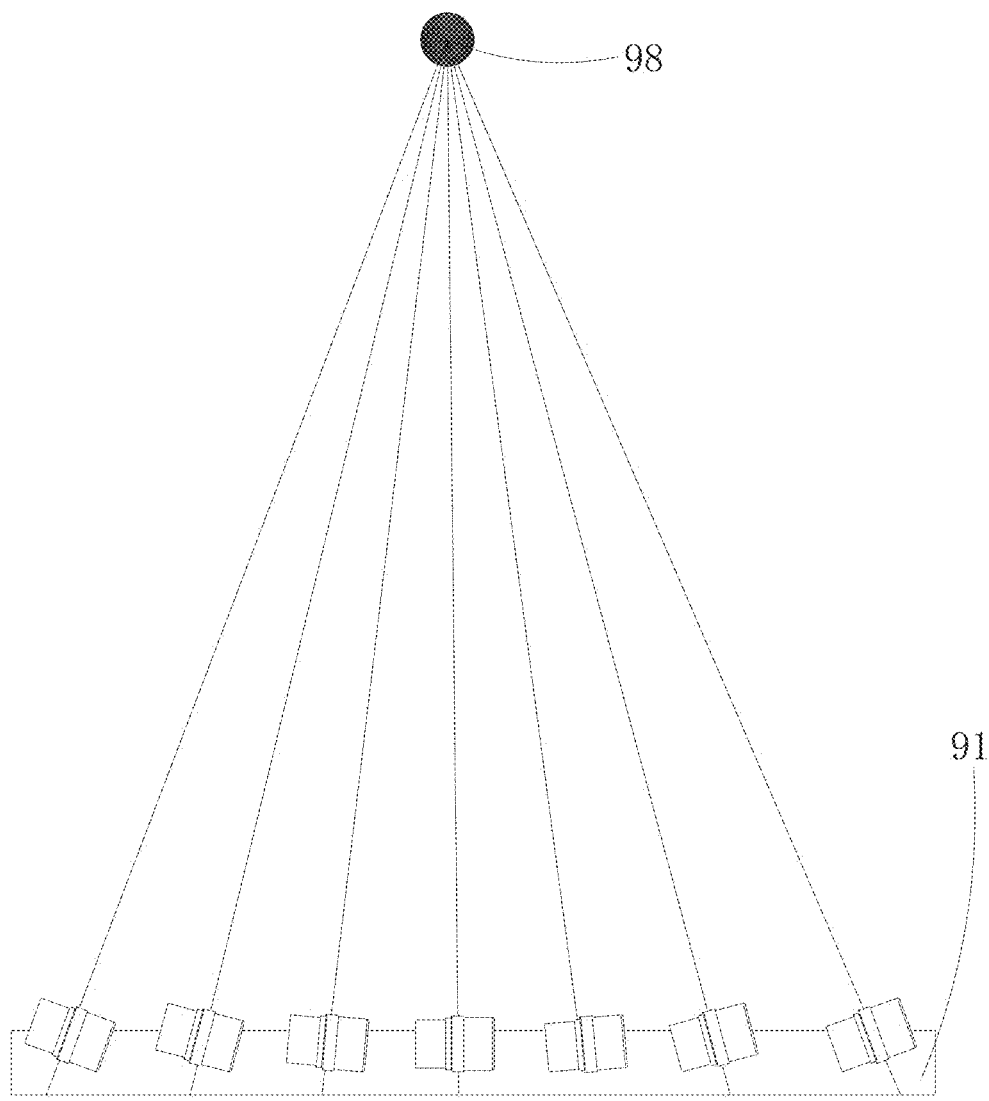
FIG. 36 is another structural schematic diagram of a sterilization system according to embodiments of the present disclosure.
Figure 37:
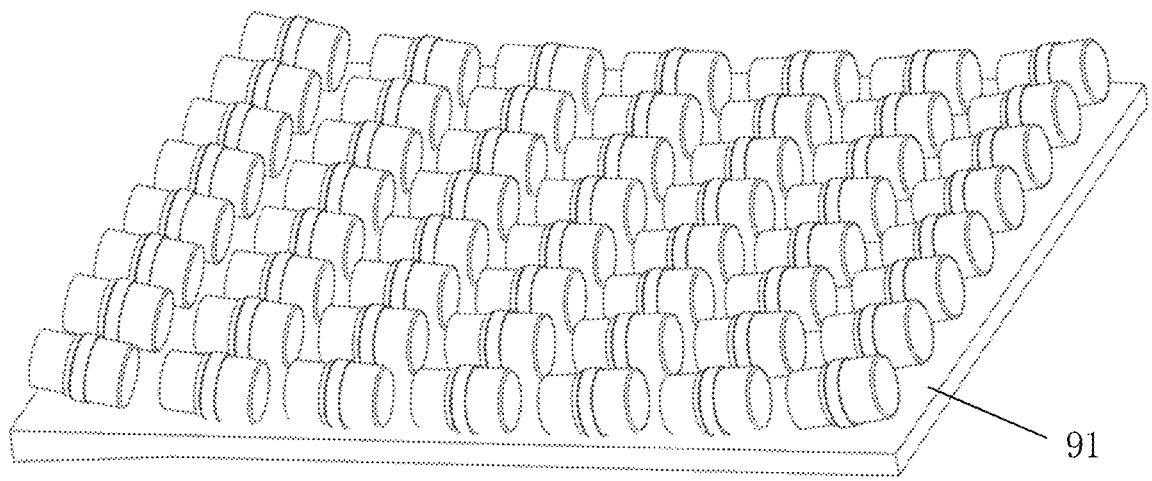
FIG. 37 is another structural schematic diagram of a bearing frame of a sterilization system according to embodiments of the present disclosure.

Further, please refer to FIG. 31, in one alternative embodiment, the main housing 61 may also be provided with a third counterpoint structure 64. The third counterpoint structure 64 is used for counterpoint fit with a fourth counterpoint structure 94 on the bearing frame 91 of the sterilization system, such that the orientation of the detector may be fixed, facilitating the sterilization for the detector by using the irradiation ray in the preset direction. The third counterpoint structure 64 may be a counterpoint groove. The fourth counterpoint structure 94 may be a counterpoint bulge. It can be understood that, as shown in FIG. 32, in another alternative embodiment, when the detector is not provided with the outer package, the third counterpoint structure 64 may be disposed on the outer surface (such as the outermost housing) of the detector.

Please combine with FIGS. 1-32 and refer to FIGS. 33-44, embodiments of the present disclosure further provide a sterilization system, and the sterilization system includes a bearing frame 91, and the bearing frame 91 is used for cooperating with the irradiation source 98 for sterilization; and the bearing frame 91 is located on one side of the irradiation source 98, one side of the bearing frame 91 that faces the irradiation source 98 is provided with a plurality of bearing portions, and each bearing portion can place one detector of any embodiment above.

When the detector is placed on the bearing portions, the bearing portions are used for correcting the orientation of the detector, such that the shielding assembly in the detector is located on the path that the irradiation source 98 is emitted to the detector.

The irradiation source 98 can emit various types of irradiation rays, including but being not limited to an X-ray, an electronic beam and a gamma ray.

When a plurality of detectors are subjected to irradiation for sterilization at once, the plurality of detectors may be placed in different bearing portions of the bearing frame 91. Since the rays emitted from the irradiation source 98 are in multiple directions, to ensure that each detector can be exposed to the irradiation ray, the bearing frame 91 is used for correcting the orientation of the detector located therein in this embodiment, to ensure that the shielding assembly or the shielding block 80 can implement the shielding effect correctly, that is, the total-shadow shielding zone 801 that wraps the sensitive element 221 and is not involved by the irradiation ray is formed.

Further, in this embodiment, a center of the bearing frame 91 is set correspondingly to the irradiation source 98;

the bearing portions may be bearing slots disposed in the bearing frame 91, the bearing slots in the middle of the bearing frame 91 are disposed perpendicularly, and other bearing slots adjacent to the middle bearing slots tilt towards one side of the irradiation source 98; and the farther the bearing slots are from the irradiation source 98, the greater a tilt angle is.

Specifically, the bearing slots in the middle of the bearing frame 91 directly face the irradiation source 98, an included angle formed by the irradiation ray emitted from the irradiation source 98 and the surface of the bearing frame 91 is a right angle, so the bearing slots are perpendicularly disposed. The farther from the irradiation source 98, the smaller the included angle formed by the irradiation ray emitted from the irradiation source 98 and the surface of the bearing frame 91 is, relatively adjusting the tilt angles of the bearing slots enables the central axes of all bearing slots can be all emitted to the irradiation source 98, to ensure that the shielding assembly or the shielding block 80 can implement the shielding effect correctly, that is, the total-shadow shielding zone 801 that wraps the sensitive element 221 and is not involved by the irradiation ray is formed.

Specifically, the placement mode of the detector is adjusted according to the forming mode and position of the total-shadow shielding zone, and the detector can be placed in the bearing frame 91 in a basically perpendicular way or placed in the bearing frame 91 in a basically horizontal way.

Figure 38:
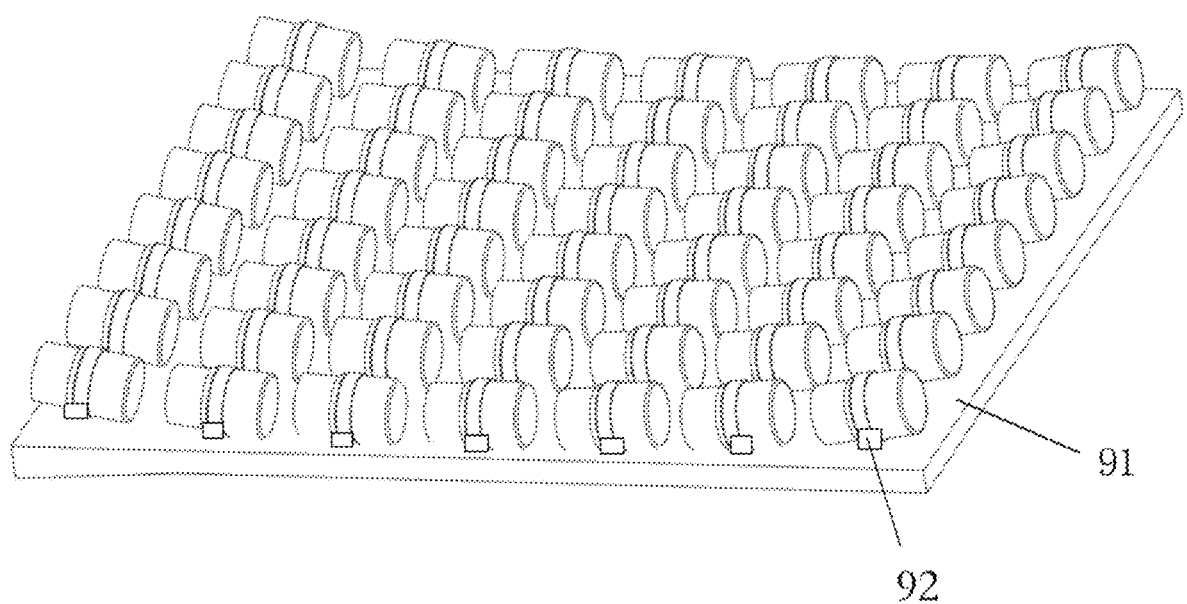
FIG. 38 is a yet another structural schematic diagram of a bearing frame of a sterilization system according to embodiments of the present disclosure.
Figure 39:
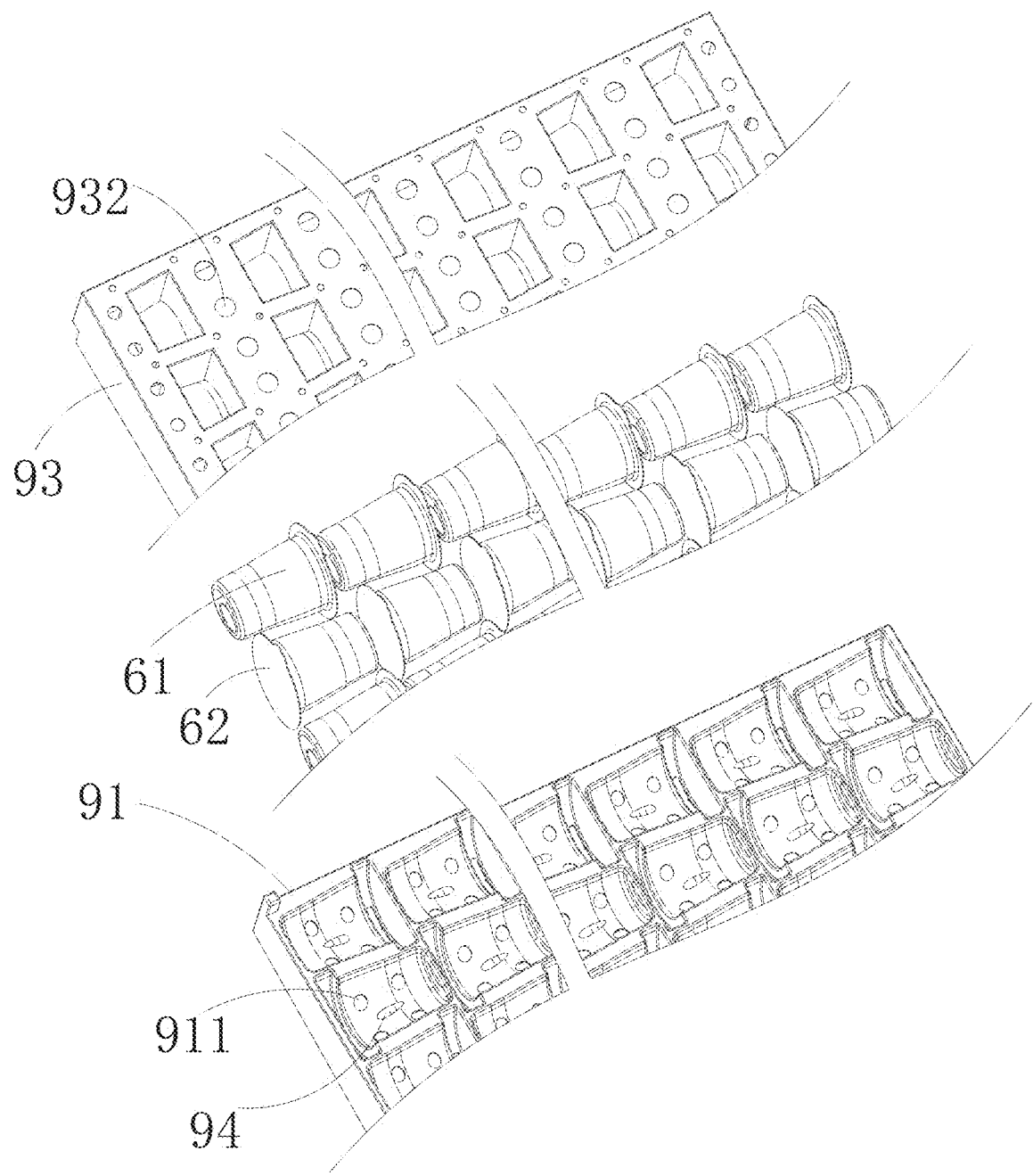
FIG. 39 is an exploded view of a partial structure of another structure of a sterilization system according to embodiments of the present disclosure.
Figure 40:
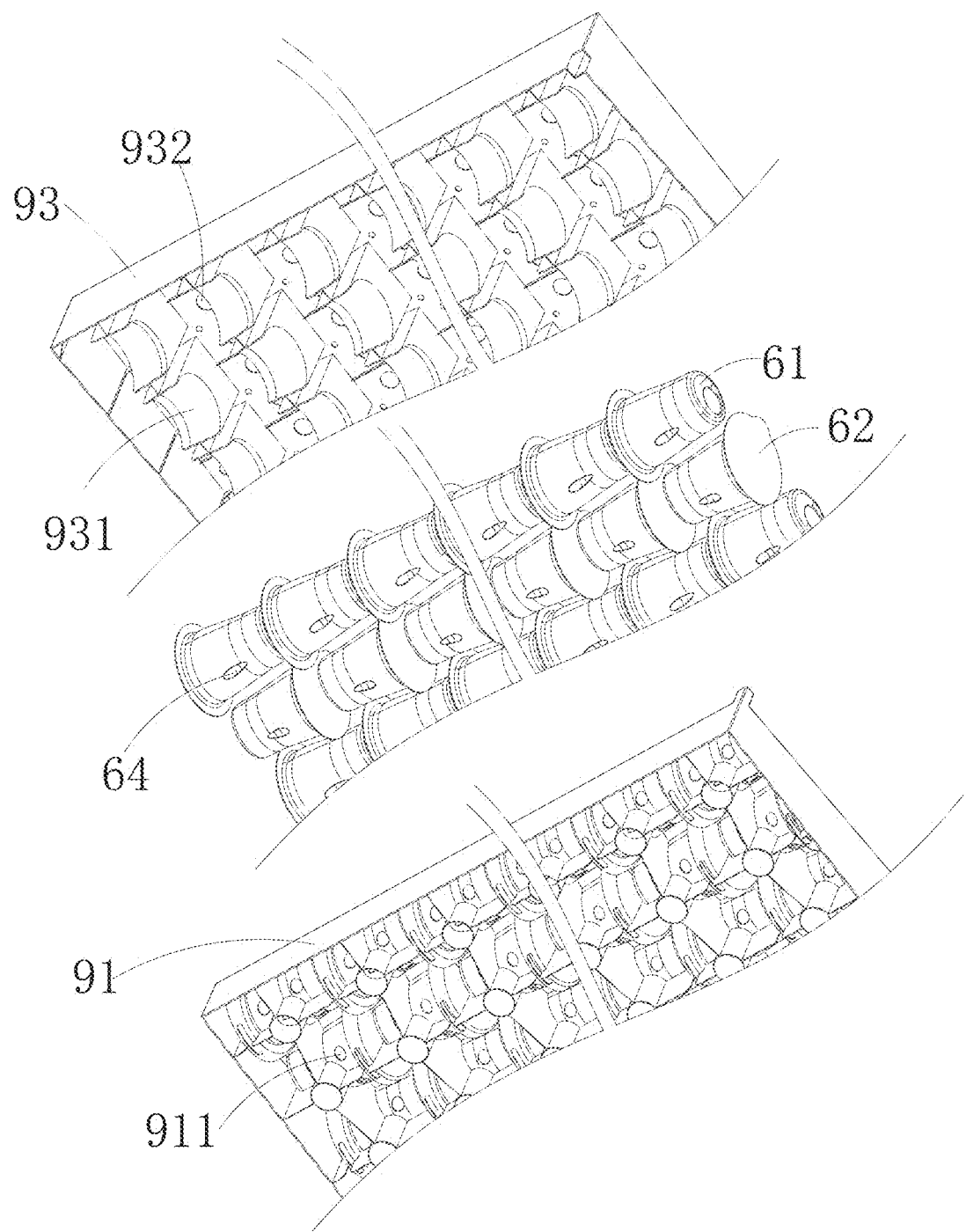
FIG. 40 is an exploded view in another angle of a partial structure of a sterilization system shown in FIG. 39.
Figure 41:
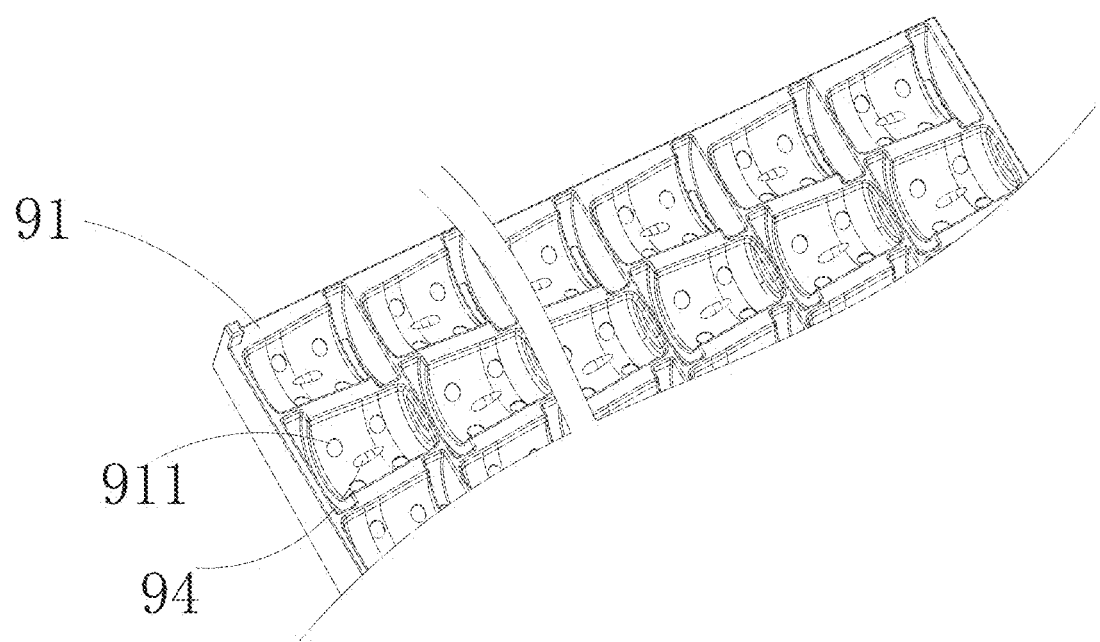
FIG. 41 is a schematic diagram of a bearing frame of a sterilization system shown in FIG. 39.
Figure 42:
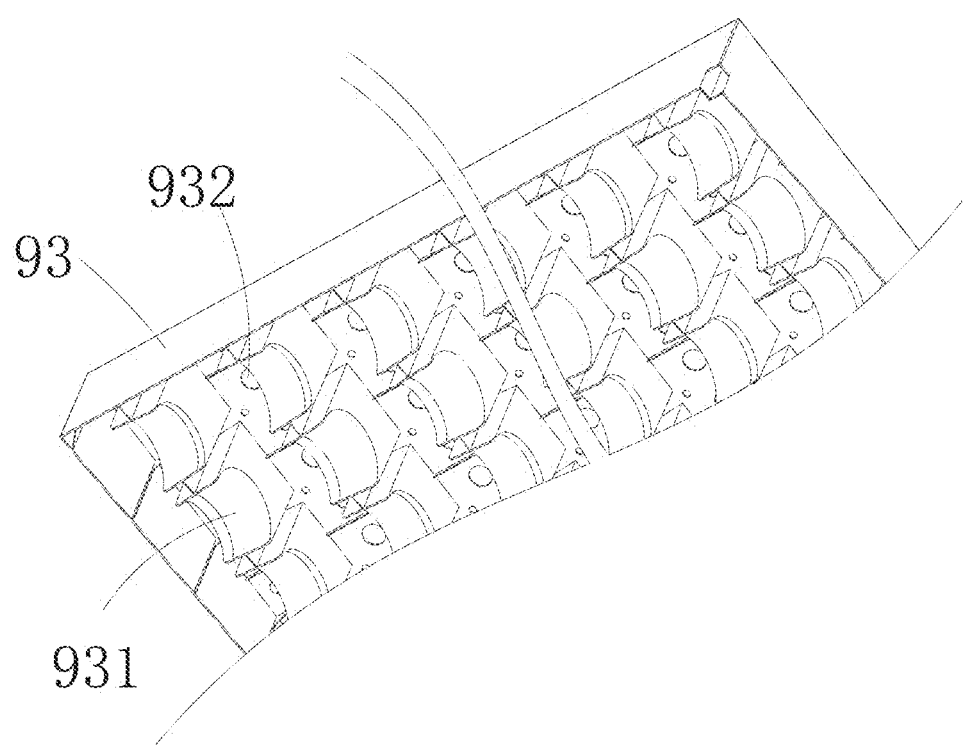
FIG. 42 is a schematic diagram of a cover plate of a sterilization system shown in FIG. 39.
Figure 43:
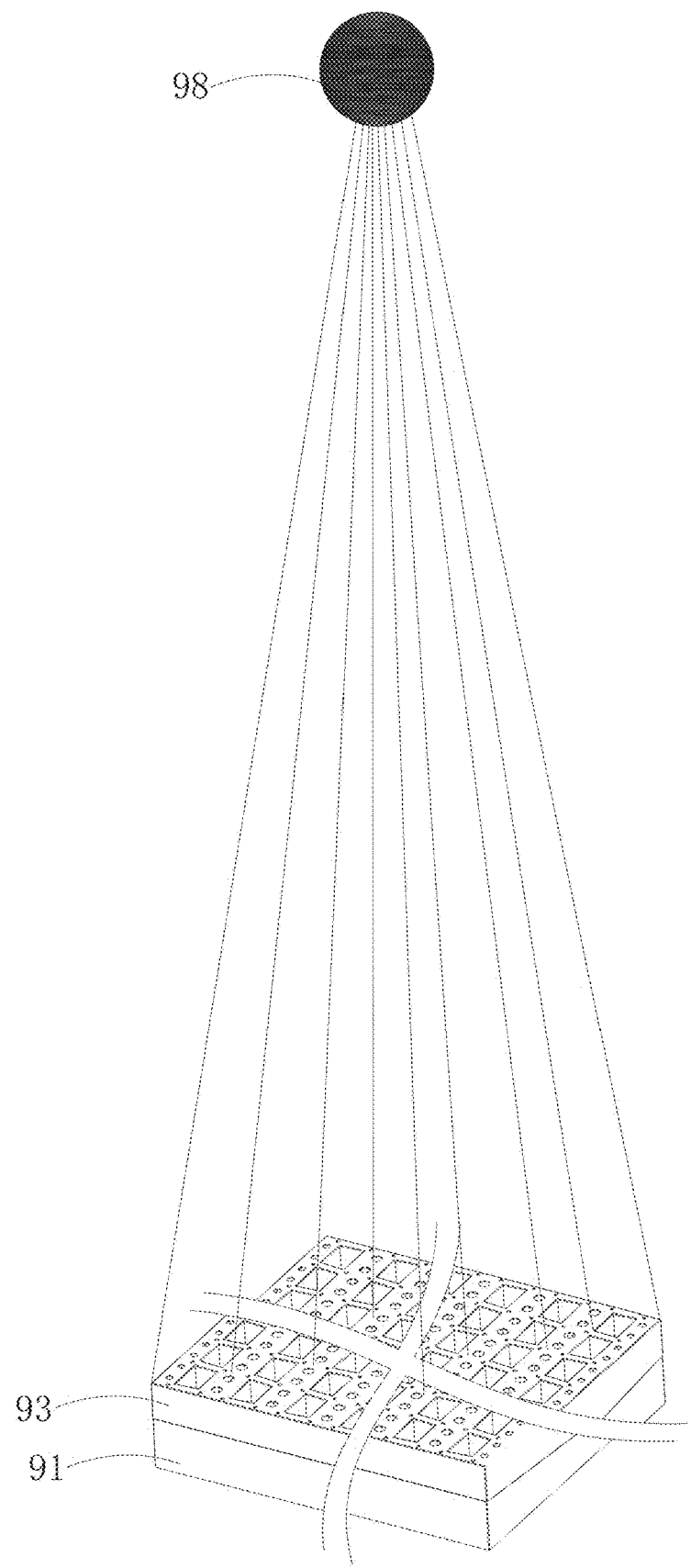
FIG. 43 is a structural schematic diagram of a sterilization system shown in FIG. 39.
Figure 44:
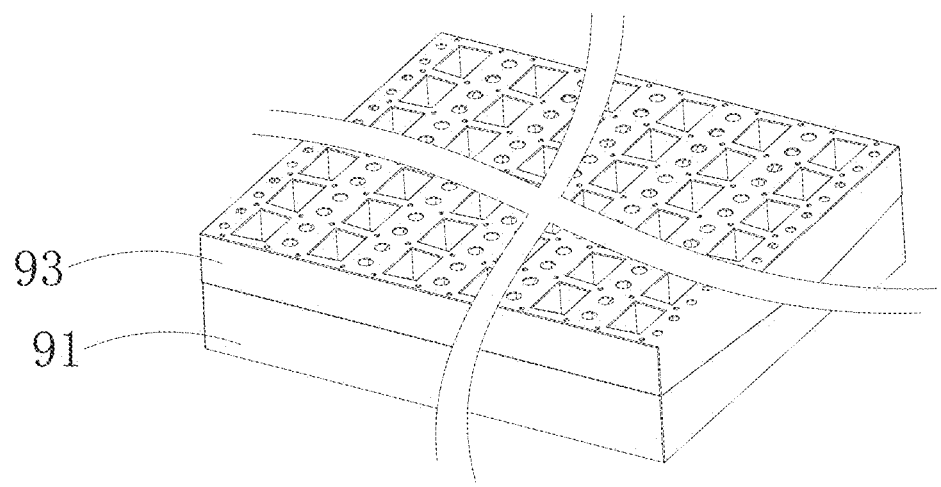
FIG. 44 is a combined schematic diagram of a bearing frame and a cover plate of a sterilization system shown in FIG. 39.

Further, please refer to FIG. 38, in yet another embodiment, the sterilization system may also include at least one fastener 92 of a magnetic suction fastener and a clip fastener, and the fastener 92 is used for fixing the detector on the bearing frame.

Please combine with FIGS. 39-44, embodiments of the present disclosure further provide a sterilization system, the sterilization system has the structure that is basically the same as that of the sterilization system in the above embodiments, where the components with the structures that are basically the same adopt the same number, the above components are not repeatedly described any more, and the key part of the sterilization system provided by this embodiment and the part different from other embodiments are mainly described below.

In this embodiment, the bearing portions are also provided with a plurality of first cooling holes 911; the sterilization system further includes a cover plate 93, and the cover plate 93 is used for covering one side where the detector is located to fix the detector in cooperation with the bearing portions; and the cover plate 93 has a counterpoint slot 931 for accommodating at least part of the detector, and a plurality of second cooling holes 932.

Further, the main housing 61 of the outer package may also be provided with a third counterpoint structure 64. The third counterpoint structure 64 is used for counterpoint fit with a fourth counterpoint structure 94 on the bearing frame 91 of the sterilization system, such that the orientation of the detector may be fixed, facilitating the sterilization for the detector by using the irradiation ray in the preset direction. In this embodiment, the third counterpoint structure 64 is a counterpoint groove, and the fourth counterpoint structure 94 is a counterpoint bulge. It can be understood that, as shown in FIG. 32, in another alternative embodiment, when the detector is not provided with the outer package, the third counterpoint structure 64 may be disposed on the outer surface (such as the outermost housing) of the detector.

Specifically, in this embodiment, the main housing 61 is also provided with a first counterpoint structure 63, the bottom (such as on the second outer shell 52) of the detector is provided with a second counterpoint structure 56, and the second counterpoint structure 56 is in counterpoint fit with the first counterpoint structure 63, such that the detector can be disposed in the main housing 61 according to the preset orientation. Such setting can ensure that the sensitive element 221 can be located in the scope of the total-shadow shielding zone 801 when the irradiation ray irradiates the detector for sterilization, thus achieving the protection to the sensitive element 221.

Other compositions for the detector and sterilization system in the above embodiments can adopt various technical solutions that are known by those skilled in the art now or in the future, and detailed descriptions are not made here.

In the description of the present disclosure, It is to be understood that, The terms "center", "longitudinal", "transverse", "upper", "lower", "front", "rear", "left", "right", "vertical", "horizontal", "top", "bottom", "inner", "outer", "clockwise", "counterclockwise", and the like indicate azimuth or positional relationships based on the azimuth or positional relationships shown in the drawings, For purposes of convenience only of describing the present disclosure and simplifying the description, Rather than indicating or implying that the indicated device or element must have a particular orientation, be constructed and operated in a particular orientation, therefore, not to be construed as limiting the present disclosure.

In addition, The terms "first" and "second" are used for descriptive purposes only, While not to be construed as indicating or implying relative importance or implicitly specifying the number of technical features indicated thereby, features defining "first," "second," and "second" may explicitly or implicitly include one or more of the described features. In the description of the present disclosure, "multiple" means two or more unless explicitly specified otherwise.

In the description of the present disclosure, it is to be noted that unless otherwise expressly specified and defined, the terms "mounted", "connected", and "connected" are to be construed broadly, for example, as either a fixed connection, or a detachable connection, or an integral connection, either a mechanical connection, or an electrical connection. The specific meaning of the above term in the present disclosure will be understood by those of ordinary skill in the art depending on the particular circumstances, either directly or indirectly via an intermediate medium, communication between the two elements, or interaction between the two elements. The specific meanings of these terms in the present disclosure will be understood by those of ordinary skill in the art as the case may be.

In the present disclosure, unless specific regulation and limitation otherwise, the first feature "onto" or "under" the second feature may include the direct contact of the first feature and the second feature, or may include the contact of the first feature and the second feature through other features between them instead of direct contact. Moreover, the first feature "onto", "above" and "on" the second feature includes that the first feature is right above and obliquely above the second feature, or merely indicates that the horizontal height of the first feature is higher than the second feature. The first feature "under", "below" and "down" the second feature includes that the first feature is right above and obliquely above the second feature, or merely indicates that the horizontal height of the first feature is less than the second feature.

Many different implementation modes or examples are provided in the above disclosure, so as to implement different structures of the present disclosure. To simplify the disclosure of the present disclosure, the components and setting of specific examples are described above. Of course, they are merely exemplary, and not intended to limit the present disclosure. In addition, the reference figures and/or reference letters may be repeated in different examples of the present disclosure, and this repetition is for the purpose of simplification and clarity, and does not indicate the discussion for the relation between various implementation modes and/or settings by itself.

In conclusion, the above are only the specific implementation modes of the present disclosure, but the scope of protection of the present disclosure is not limited to this. Those skilled in the art can easily think of various changes or replacements within the scope of the technology disclosed in the present disclosure, which shall be covered by the scope of protection of the present disclosure. Therefore, the scope of protection of this application should be subject to the scope of protection of the appended claims.

What is claimed is:

1. A detector, comprising a housing assembly, a detection assembly and a shielding assembly, wherein
the detection assembly comprises a first housing, a detection circuit board and a probe, the detection circuit board is disposed in the first housing and electrically connected with the probe, the detection circuit board comprises a sensitive element, and a first end of the probe is fixed in the first housing while a second end stretches out of the first housing;

the housing assembly comprises a collision housing and a pressing portion that are capable of sliding in relative to each other, the detection assembly is located below a bottom of the pressing portion, the collision housing is used for abutting against a sampling part, and the pressing portion is used for driving the detection assembly to move towards the sampling part, so as to pierce the probe into the sampling part for detection; and when the detector is sterilized through an irradiation ray, the shielding assembly is used for blocking part of the irradiation ray, to form a total-shadow shielding zone for protecting the sensitive element, and at least part of the total-shadow shielding zone is configured as a sealing area for preventing an external object from entering;

wherein the first housing comprises a bearing shell and a cover body, the bearing shell is hermetically connected with the cover body and forms a sealed storage cavity, the detection circuit board is located in the storage cavity, and the sealing area comprises the storage cavity; and wherein the first housing further comprises a sealing element, the bearing shell is hermetically connected with the cover body through the sealing element, and the sealing element comprises a sealant, a sealing rubber ring or a combination of a sealant and a sealing rubber ring.

2. The detector according to claim 1, wherein the bearing shell comprises a bearing plate and a side wall structure connected with the bearing plate, the side wall structure is provided with a sealing slot, at least part of the sealing element is located in the sealing slot, the cover body comprises a main cover body and a raised structure that is connected with the main cover body and extends towards one side of the bearing plate, and the raised structure is used for resisting and connecting the sealing element.

3. The detector according to claim 1, wherein the shielding assembly is disposed on the detection circuit board, the shielding assembly and the sensitive element are arranged on a path that an irradiation source for sterilization is emitted to the detector, such that the shielding assembly blocks a radiation of the irradiation source to be emitted to the sensitive element.

4. The detector according to claim 3, wherein the detection circuit board further comprises a battery module or an electronic device, the battery module or the electronic device, the shielding assembly and the sensitive element are all disposed on the detection circuit board, the shielding assembly and the sensitive element are arranged on a path that the irradiation source for sterilization is emitted to the detector, such that the battery module or the electronic device and the shielding assembly block the radiation of the irradiation source to be emitted to the sensitive element together.

5. The detector according to claim 3, wherein the irradiation direction of the radiation is perpendicular to the pressing direction of the pressing portion.

6. The detector according to claim 1, wherein the detection assembly further comprises a shielding sheet, the shielding sheet is disposed in the first housing, the shielding sheet is located on a path that the irradiation ray is emitted to the sensitive element, and forms the total-shadow shielding zone for protecting the sensitive element.

7. A sterilization system, wherein the sterilization system comprises a bearing frame, and the bearing frame is used for cooperating with an irradiation source for sterilization;

the bearing frame is located on one side of the irradiation source, one side of the bearing frame that faces the irradiation source is provided with a plurality of bearing portions, and each bearing portion is used for placing one detector according to claim 1; and when the detector is placed on the bearing portions, the bearing portions are used for correcting an orientation of the detector, such that the shielding assembly in the detector is located on a path that the irradiation source is emitted to the detector.

8. The sterilization system according to claim 7, wherein a center of the bearing frame is disposed correspondingly to the irradiation source;

the bearing portions are bearing slots disposed in the bearing frame, the bearing slots in the middle of the bearing frame are disposed perpendicularly, and other bearing slots adjacent to the middle bearing slots tilt towards one side of the irradiation source; and the farther the bearing slots are from the irradiation source, the greater a tilt angle thereof is.

9. The sterilization system according to claim 7, wherein the sterilization system further comprises at least one fastener of a magnetic suction fastener and a clip fastener, the fastener is used for fixing the detector on the bearing frame, and the bearing portions are also provided with a plurality of first cooling holes; the sterilization system further comprises a cover plate, and the cover plate is used for covering one side where the detector is located to fix the detector in cooperation with the bearing portions; and the cover plate has a counterpoint slot for accommodating at least part of the detector, and a plurality of second cooling holes.

10. The sterilization system according to claim 7, wherein the bearing portions are also provided with counterpoint structures that are used in cooperation with the detector or another counterpoint structure on the outer package of the detector, such that the detector is capable of being set according to a preset orientation; and when the outer package of the detector has the another counterpoint structure, the detector has a first counterpoint structure, and the outer package has a second counterpoint structure used in cooperation with the first counterpoint structure, such that the detector is set in the outer package according to the preset orientation.

11. The detector according to claim 1, wherein the shielding assembly comprises a shielding frame, the shielding frame comprises a connecting plate and two side baffles, the connecting plate pass through a fixed hole of the detection circuit board, the two side baffles are separately fixed to two opposite ends of the connecting plate, and the sensitive element is located between the two side baffles.

12. The detector according to claim 1, wherein the shielding assembly comprises a shielding block having a density greater than 1,000 kg/m$^3$.

13. The detector according to claim 2, wherein the collision housing comprises a first barrel-shaped bracket;

the pressing portion comprises a pressing shell, a second barrel-shaped bracket, a support bracket and an elastic element;

the first barrel-shaped bracket is slidingly and partially located in the pressing shell, and an inner wall of the first barrel-shaped bracket is provided with a raised portion;

the second barrel-shaped bracket is slidingly sleeved in the first barrel-shaped bracket, the second barrel-shaped bracket comprises a barrel-shaped structure and a base plate at a bottom thereof, the barrel-shaped structure is provided with a guide hole along an axial direction, a positioning hole is provided on a path of the guide hole, a plurality of connecting portions extend on an outer edge of the base plate, and the plurality of connecting portions are fixedly connected with the pressing shell;

the support bracket is located in the barrel-shaped structure, an elastic resisting portion extends outside the support bracket, and the guide needle is connected with the support bracket;

the elastic element is compressed between the base plate and a top of the support bracket;

in an initial state, the elastic element is located in a compressed state, and the elastic resisting portion is located in the positioning hole; and under the action of an external force, the pressing shell drives the second barrel-shaped bracket to move in relative to the first barrel-shaped bracket, such that the raised portion moves along the guide hole; when the second barrel-shaped bracket moves to a first preset position in relative to the first barrel-shaped bracket, the guide needle guides the probe to be pierced into the sampling part; and when the second barrel-shaped bracket moves to a second preset position in relative to the first barrel-shaped bracket, the raised portion extrudes the elastic resisting portion out of the positioning hole, the elastic element is released, and the support bracket drives the guide needle to leave the sampling part.

14. The detector according to claim 13, wherein the first housing has a cut-through hole, one end of the probe is located in the cut-through hole and stretches into the first housing by passing through a connector of a hole wall of the cut-through hole to be electrically connected with the detection circuit board, the other end of the probe stretches out of the cut-through hole and extends towards a direction away from the pressing portion, the guide needle comprises a connecting rod and a needle body connected with the connecting rod, the connecting rod is connected with the support bracket, and the needle body is provided with a through hole that accommodates the probe and is slidingly connected with the probe.

15. The sterilization system according to claim 7, wherein the shielding assembly comprises a shielding frame, the shielding frame comprises a connecting plate and two side baffles, the connecting plate pass through a fixed hole of the detection circuit board, the two side baffles are separately fixed to two opposite ends of the connecting plate, and the sensitive element is located between the two side baffles.

16. The sterilization system according to claim 7, wherein the shielding assembly comprises a shielding block having a density greater than 1,000 kg/m$^3$.

17. The sterilization system according to claim 7, wherein the shielding assembly is disposed on the detection circuit board, the shielding assembly and the sensitive element are arranged on a path that an irradiation source for sterilization is emitted to the detector, such that the shielding assembly blocks a radiation of the irradiation source to be emitted to the sensitive element, the detection circuit board further comprises a battery module or an electronic device, the battery module or the electronic device, the shielding assembly and the sensitive element are all disposed on the detection circuit board, the shielding assembly and the sensitive element are arranged on the path that the irradiation source for sterilization is emitted to the detector, such that the battery module or the electronic device and the shielding assembly block the radiation of the irradiation source to be emitted to the sensitive element together.

18. The sterilization system according to claim 7, wherein the shielding assembly is disposed on the detection circuit board, the shielding assembly and the sensitive element are arranged on a path that an irradiation source for sterilization is emitted to the detector, such that the shielding assembly blocks a radiation of the irradiation source to be emitted to the sensitive element, an irradiation direction of the radiation is different from a pressing direction of the pressing portion, and the irradiation direction of the radiation is perpendicular to the pressing direction of the pressing portion.

19. A detector, comprising a housing assembly, a detection assembly and a shielding assembly, wherein the detection assembly comprises a first housing, a detection circuit board and a probe, the detection circuit board is disposed in the first housing and electrically connected with the probe, the detection circuit board comprises a sensitive element, and a first end of the probe is fixed in the first housing while a second end stretches out of the first housing;

the housing assembly comprises a collision housing and a pressing portion that are capable of sliding in relative to each other, the detection assembly is located below a bottom of the pressing portion, the collision housing is used for abutting against a sampling part, and the pressing portion is used for driving the detection assembly to move towards the sampling part, so as to pierce the probe into the sampling part for detection; and when the detector is sterilized through an irradiation ray, the shielding assembly is used for blocking part of the irradiation ray, to form a total-shadow shielding zone for protecting the sensitive element;

wherein the probe is brought into the sampling part through a guide needle;

the collision housing comprises a first barrel-shaped bracket;

the pressing portion comprises a pressing shell, a second barrel-shaped bracket, a support bracket and an elastic element;

the first barrel-shaped bracket is slidingly and partially located in the pressing shell, and an inner wall of the first barrel-shaped bracket is provided with a raised portion;

the second barrel-shaped bracket is slidingly sleeved in the first barrel-shaped bracket, the second barrel-shaped bracket comprises a barrel-shaped structure and a base plate at a bottom thereof, the barrel-shaped structure is provided with a guide hole along an axial direction, a positioning hole is provided on a path of the guide hole, a plurality of connecting portions extend on an outer edge of the base plate, and the plurality of connecting portions are fixedly connected with the pressing shell;

the support bracket is located in the barrel-shaped structure, an elastic resisting portion extends outside the support bracket, and the guide needle is connected with the support bracket;

the elastic element is compressed between the base plate and a top of the support bracket;

in an initial state, the elastic element is located in a compressed state, and the elastic resisting portion is located in the positioning hole; and under the action of an external force, the pressing shell drives the second barrel-shaped bracket to move in relative to the first barrel-shaped bracket, such that the raised portion moves along the guide hole; when the second barrel-shaped bracket moves to a first preset position in relative to the first barrel-shaped bracket, the guide needle guides the probe to be pierced into the sampling part; and when the second barrel-shaped bracket moves to a second preset position in relative to the first barrel-shaped bracket, the raised portion extrudes the elastic resisting portion out of the positioning hole, the elastic element is released, and the support bracket drives the guide needle to leave the sampling part.

20. The detector according to claim 19, wherein the first housing has a cut-through hole, one end of the probe is located in the cut-through hole and stretches into the first housing by passing through a connector of a hole wall of the cut-through hole to be electrically connected with the detection circuit board, the other end of the probe stretches out of the cut-through hole and extends towards a direction away from the pressing portion, the guide needle comprises a connecting rod and a needle body connected with the connecting rod, the connecting rod is connected with the support bracket, and the needle body is provided with a through hole that accommodates the probe and is slidingly connected with the probe.

\* \* \* \* \*